United States Patent
Noda et al.

(10) Patent No.: US 10,381,221 B2
(45) Date of Patent: Aug. 13, 2019

(54) SUBSTRATE PROCESSING METHOD, SUBSTRATE PROCESSING APPARATUS AND A COMPUTER-READABLE STORAGE MEDIUM

(71) Applicant: Tokyo Electron Limited, Tokyo (JP)

(72) Inventors: Yasuaki Noda, Koshi (JP); Tadashi Nishiyama, Koshi (JP)

(73) Assignee: Tokyo Electron Limited, Minato-Ku (JP)

( * ) Notice: Subject to any disclaimer, the term of this patent is extended or adjusted under 35 U.S.C. 154(b) by 83 days.

(21) Appl. No.: 15/437,885

(22) Filed: Feb. 21, 2017

(65) Prior Publication Data

US 2017/0243738 A1    Aug. 24, 2017

(30) Foreign Application Priority Data

Feb. 22, 2016  (JP) ................. 2016-031369

(51) Int. Cl.
*G03F 7/20* (2006.01)
*H01L 21/68* (2006.01)
(Continued)

(52) U.S. Cl.
CPC .......... *H01L 21/0274* (2013.01); *B05D 1/005* (2013.01); *G03F 7/168* (2013.01); *G03F 7/20* (2013.01); *G03F 7/2028* (2013.01); *G03F 7/26* (2013.01); *G06T 7/0008* (2013.01); *G06T 7/60* (2013.01); *H01L 21/6715* (2013.01); *H01L 21/67173* (2013.01); *H01L 21/67253* (2013.01); *H01L 21/67288* (2013.01);
(Continued)

(58) Field of Classification Search
CPC ............. H01L 21/6715; H01L 21/0274; H01L 21/67253; H01L 21/67288; H01L 21/681; H01L 21/68714; H01L 22/12; H01L 22/20; G03F 7/20; G03F 7/26; G03F 7/168; G03F 7/2028; G06T 7/0008; G06T 7/60; G06T 2207/30148; B05D 1/005
USPC ....................................................... 427/240
See application file for complete search history.

(56) References Cited

U.S. PATENT DOCUMENTS

| | | | |
|---|---|---|---|
| 2009/0214963 A1* | 8/2009 | Tadokoro | G03F 7/705 430/30 |
| 2015/0255355 A1* | 9/2015 | Kodama | H01L 22/20 438/7 |
| 2016/0209763 A1* | 7/2016 | Saito | G03F 7/2028 |

FOREIGN PATENT DOCUMENTS

| | | |
|---|---|---|
| JP | 11-333355 | 12/1999 |
| JP | 2002-158166 | 5/2002 |

* cited by examiner

*Primary Examiner* — Kirsten Jolley
(74) *Attorney, Agent, or Firm* — Burr & Brown, PLLC

(57) ABSTRACT

A processing method in one embodiment includes: a step that takes an image of the end face of a reference substrate, whose warp amount is known, over the whole periphery thereof using a camera to obtain shape data of the end face of the reference substrate over the whole periphery of the reference substrate; a step that takes an image of the end face of a substrate over the whole periphery thereof using a camera to obtain shape data of the end face of the substrate over the whole periphery of the substrate; a step that calculates warp amount of the substrate based on the obtained shape data; a step that forms a resist film on a surface of the substrate; a step that determines the supply position from which an organic solvent is to be supplied to a peripheral portion of the resist film and dissolves the peripheral portion by the solvent supplied from the supply position to remove the same from the substrate.

14 Claims, 29 Drawing Sheets

(51) Int. Cl.
*H01L 21/027* (2006.01)
*B05D 1/00* (2006.01)
*G03F 7/26* (2006.01)
*G06T 7/60* (2017.01)
*H01L 21/67* (2006.01)
*H01L 21/687* (2006.01)
*H01L 21/66* (2006.01)
*G06T 7/00* (2017.01)
*G03F 7/16* (2006.01)

(52) U.S. Cl.
CPC ...... *H01L 21/681* (2013.01); *H01L 21/68714* (2013.01); *H01L 22/20* (2013.01); *G06T 2207/30148* (2013.01); *H01L 22/12* (2013.01)

SUBSTRATE PROCESSING METHOD, SUBSTRATE PROCESSING APPARATUS AND A COMPUTER-READABLE STORAGE MEDIUM

CROSS-REFERENCE TO RELATED APPLICATIONS

This application is based upon and claims the benefit of priority from Japanese Patent Application No. 2016-031369, filed on Feb. 22, 2016, the entire contents of which are incorporated herein by reference.

BACKGROUND OF THE INVENTION

Field of the Invention

The present invention relates to a substrate processing method, a substrate processing apparatus and a computer-readable storage medium.

Background Art

At present, when a substrate (e.g., a semiconductor wafer) is micromachined to manufacture a semiconductor device, a pattern (patterned projections/recesses) (e.g., a resist pattern) is generally formed on a substrate by means of a photolithography technique. The process for forming a resist pattern on a semiconductor wafer includes, for example, a resist-film forming step that forms a resist film (coating film) on a surface of a wafer, an exposure step that exposes the resist film along a predetermined pattern, and a developing step that develops the exposed resist film by reacting the same and a developer.

In general, a spin coating method that drops a resist liquid onto a surface of a wafer while rotating the wafer is employed to perform the resist-film forming step. Thus, in general, a resist film is formed all over the surface of the wafer. When such a wafer W is transported by a transport arm, the resist film adheres to the transport arm upon gripping of the peripheral portion of the wafer W by the transport arm. In this case, a succeeding wafer may be contaminated by residue of the resist film adhering to the transport arm. Thus, in some cases, a periphery removal process for removing a resist film present on the peripheral portion of a wafer is performed.

Patent Document 1 (JP11-333355A) discloses, as an example of the periphery removal process, a method for removing a peripheral portion of a resist film along a periphery of a wafer (called "edge rinsing process"). The method supplies, after forming the resist film on the wafer surface, an organic solvent to a portion of the resist film having been solidified and positioned on the peripheral portion of the wafer (i.e., the peripheral portion of the resist film) while rotating the wafer. Patent Document 2 (JP2002-158166A) discloses, as another example of the periphery removal process, a method (periphery exposing and developing process) for removing a peripheral portion of a resist film along the periphery of a wafer. The method exposes the peripheral area of the wafer inwardly extending from the periphery of the wafer and having a predetermined radial width, and develops the same area.

Since a wafer is manufactured through various steps, the wafer may be warped before the wafer is subjected to a certain fine processing step. In addition, in order to form a resist film on a surface of a wafer, the wafer is subjected to a heating process and a cooling process after applying a resist liquid to the surface of the wafer. Thus, the wafer may be warped due to the heating and/or cooling of the wafer. Especially in recent years, the development of 3D NAND flash memories has been progressing. Since the memory is manufactured through many steps each for forming a resist film, a wafer is repeatedly subjected to a heating process and a cooling process. Thus, the warp of the wafer may be as significantly large as about several hundred micrometers to one millimeter.

When a warped wafer is rotating to be processed, a height position of the periphery of the wafer may vary. Thus, when the edge rinsing process is performed to the periphery of the wafer, the gap between the periphery and a nozzle for supplying an organic solvent may vary. Similarly, when the periphery exposing and developing process is performed to the periphery of the wafer, the optical path length up to the periphery may vary. Thus, when the periphery removal process (edge rinsing process, periphery exposing and developing process, etc.) is performed to the warped wafer, the removal width of the peripheral portion of the resist film disadvantageously becomes non-uniform along the periphery of the wafer. For example, the removal width may not reach a target value or may exceed the target value. Particularly in recent years, further miniaturization of the pattern is required to form a highly-integrated circuit on a wafer. If a wafer has a part whose removal width of a peripheral portion of a resist film is large, high integration of circuits on one substrate is prevented.

SUMMARY OF THE INVENTION

The disclosure describes a substrate processing method, a substrate processing apparatus and a computer-readable storage medium capable of properly processing a periphery of a substrate even if the substrate is warped.

A substrate processing method in a first aspect of the present disclosure comprises a first step that takes an image of an end face of a reference substrate, whose warp amount is known, over a whole periphery of the reference substrate by means of a camera; a second step that performs image processing of the image taken in the first step, thereby to obtain shape data of the end face of the reference substrate over a whole periphery of the reference substrate; a third step that takes an image of an end face of a process substrate over a whole periphery of the process substrate by means of a camera; a fourth step that performs image processing of the image taken in the third step, thereby to obtain shape data of the end face of the process substrate over a whole periphery of the process substrate; a fifth step that calculates a warp amount of the process substrate based on the shape data obtained in the second step and the shape data obtained in the fourth step; a sixth step that supplies a coating liquid to a surface of the process substrate thereby to form a coating film on the surface of the process substrate; a seventh step that determines a supply position from which an organic solvent is to be supplied to a peripheral portion of the coating film, based on the warp amount calculated in the fifth step, and supplies the organic solvent from the supply position to dissolve the peripheral portion of the coating film and remove the same from the process substrate.

In the substrate processing method in the first aspect, the fifth step calculates a warp amount of the process substrate, and the seventh step determines, based on the warp amount, a supply position from which an organic solvent is to be supplied to the peripheral portion of the coating film, and dissolves the peripheral portion by the organic solvent from the supply position so as to remove the same from the process substrate. Thus, since the supply position from which the organic solvent is to be supplied to the peripheral portion of the coating film can be properly determined depending on the warp amount of the process substrate, the removal width of the peripheral portion can be made more uniform. As a result, even if the process substrate is warped, the periphery of the process substrate can be properly processed. In addition, since a circuit can be formed on the surface of the process substrate at a portion close to the periphery, high integration of circuits on the process substrate is promoted whereby the process substrate can be more efficiently utilized.

The substrate processing method in the first aspect may further comprise a periphery exposure step that exposes, after the seventh step, the coating film in the peripheral portion of the surface of the process substrate at a predetermined exposure width over the whole periphery of the process substrate, wherein in the periphery exposure step the exposure width is determined based on the warp amount calculated in the fifth step. In this case, since the exposure width can be properly determined depending on the warp amount of the process substrate, the exposure width of the peripheral portion can be made more uniform. Thus, by developing the process substrate after the peripheral exposure step, the removal width of the peripheral portion can be made more uniform.

The substrate processing method in the first aspect may further comprise an eighth step that heats the coating film after the seventh step; a ninth step that takes, after the eighth step, an image of the end face of the process substrate over the whole periphery of the process substrate by means of a camera; a tenth step that performs image processing of the image taken in the ninth step, thereby to obtain shape data of the end face of the process substrate over the whole periphery of the process substrate; and an eleventh step that calculates a warp amount of the process substrate based on the shape data obtained in the second step and the shape data obtained in the tenth step; wherein the method does not perform exposure of the process substrate if the warp amount calculated in the eleventh step is greater than a threshold value. In this case, a process substrate that is difficult to be exposed by an exposure apparatus can be discriminated beforehand, so that such a process substrate can be excluded from the exposure process. Thus, the process efficiency of process substrates can be improved.

The substrate processing method in the first aspect may further comprise an eighth step that heats the coating film after the seventh step; a ninth step that takes, after the eighth step, an image of the end face of the process substrate over the whole periphery of the process substrate by means of a camera; a tenth step that performs image processing of the image taken in the ninth step, thereby to obtain shape data of the end face of the process substrate over the whole periphery of the process substrate; and an eleventh step that calculates a warp amount of the process substrate based on the shape data obtained in the second step and the shape data obtained in the tenth step; a periphery exposure step that exposes, after the ninth step, the coating film in the peripheral portion of the surface of the process substrate at a predetermined exposure width over the whole periphery of the process substrate, wherein in the periphery exposure step the exposure width is determined based on the warp amount calculated in the eleventh step. In this case, since the exposure width can be more properly determined depending on the warp amount of the process substrate that has been subjected to the heating process in the eighth step, the exposure width of the peripheral portion can be made more uniform. Thus, by developing the process substrate after the peripheral exposure step, the removal width of the peripheral portion can be made more uniform.

The substrate processing method may omit exposure of the process substrate if the warp amount calculated in the eleventh step is greater than a threshold value. In this case, a process substrate that is difficult to be exposed by an exposure apparatus can be discriminated beforehand and the process substrate can be excluded from the exposure process. Thus, the process efficiency of process substrates can be improved.

A substrate processing method in a second aspect of the disclosure comprises: a first step that takes an image of an end face of a reference substrate, whose warp amount is known, over a whole periphery of the reference substrate by means of a camera; a second step that performs image processing of the image taken in the first step, thereby to obtain shape data of the end face of the reference substrate over a whole periphery of the reference substrate; a third step that takes an image of an end face of a process substrate over a whole periphery of the process substrate by means of a camera; a fourth step that performs image processing of the image taken in the third step, thereby to obtain shape data of the end face of the process substrate over a whole periphery of the process substrate; a fifth step that calculates a warp amount of the process substrate based on the shape data obtained in the second step and the shape data obtained in the fourth step; a sixth step that supplies a coating liquid to a surface of the process substrate thereby to form a coating film on the surface of the process substrate; and a periphery exposure step that exposes the coating film in the peripheral portion of the surface of the process substrate at a predetermined exposure width over the whole periphery of the process substrate, wherein in the periphery exposure step the exposure width is determined based on the warp amount calculated in the fifth step.

In the substrate processing method in the second aspect, the fifth step calculates a warp amount of the process substrate, and in the periphery exposure step, the exposure width is determined based on the warp amount. Thus, since the exposure width can be determined depending on the warp amount of the process substrate, the exposure width of the peripheral portion can be made more uniform. Therefore, by developing the process substrate after the periphery exposure step, the removal width of the peripheral portion can be made more uniform. As a result, even if the process substrate is warped, the periphery of the process substrate can be properly processed. In addition, since a circuit can be formed on the surface of the process substrate in areas close to the periphery, higher integration of circuits on the process substrate is achieved whereby the process substrate can be more efficiently utilized.

The substrate processing method in the second aspect may further comprise a seventh step that heats the coating film after the sixth step, wherein the third, fourth and fifth steps are performed after the seventh step. In this case, since the exposure width can be more properly determined depending on the warp amount of the process substrate that has been subjected to the heating process in the seventh step, the exposure width of the peripheral portion can be made more uniform. Thus, by developing the process substrate after the periphery exposure step, the removal width of the peripheral portion can be made more uniform.

The substrate processing method may omit exposure of the process substrate if the warp amount calculated in the fifth step is greater than a threshold value. In this case, a process substrate that is difficult to be exposed by an exposure apparatus can be discriminated beforehand and such a process substrate can be excluded from the exposure process. Thus, the process efficiency of process substrates can be improved.

The reference substrate may be flat; the shape data obtained in the second step may be data on a first profile line passing through a center of the end face of the reference substrate; the shape data obtained in the fourth step may be data on a second profile line passing through a center of the end face of the process substrate; and the fifth step may calculate the warp amount of the process substrate based on the data on the first profile line and the data on the second profile line. In this case, the warp amount of the process substrate can be more easily calculated from the data on the first profile line and the data on the second profile line.

The substrate processing method in the first or second aspect may further comprise: a peripheral portion imaging step that takes an image of a peripheral portion of a surface of the process substrate by means of a camera; and an inspecting step that inspects condition of the end face of the process substrate through image processing of the image taken in the fourth step, and inspects condition of the peripheral portion of the surface of the process substrate through image processing of the image taken in the peripheral portion imaging step. In this case, a defect (for example, flaw, crack, scratch, etc.) in the vicinity of the periphery of the process substrate can be detected and the process substrate can be excluded from the various processes. Thus, the process efficiency of process substrates can be improved.

A substrate processing apparatus in an third aspect of the present disclosure comprises: a coating liquid supplying unit configured to supply a coating liquid onto a surface of a process substrate; a solvent supplying unit configured to supply a first organic solvent and a second organic solvent onto a surface of a process substrate; a first rotary holding unit configured to hold and rotate the process substrate; at least one camera; and a control unit, wherein the control unit is configured to control the substrate processing apparatus to perform a procedure including: a first step that takes an image of an end face of a reference substrate, whose warp amount is known, over a whole periphery of the reference substrate by means of said at least one camera; a second step that performs image processing of the image taken in the first step, thereby to obtain shape data of the end face of the reference substrate over a whole periphery of the reference substrate; a third step that takes an image of an end face of a process substrate over a whole periphery of the process substrate by means of said at least one camera; a fourth step that performs image processing of the image taken in the third step, thereby to obtain shape data of the end face of the process substrate over a whole periphery of the process substrate; a fifth step that calculates a warp amount of the process substrate based on the shape data obtained in the second step and the shape data obtained in the fourth step; a sixth step that controls the coating liquid supplying unit and the first rotary holding unit and supplies a coating liquid to a surface of the rotating process substrate thereby to form a coating film on the surface of the process substrate; a seventh step that controls the solvent supplying unit and the first rotary holding unit, determines a supply position from which an organic solvent is to be supplied to a peripheral portion of the coating film, based on the warp amount calculated in the fifth step, and supplies the organic solvent from the supply position to dissolve the peripheral portion of the coating film and remove the same from the rotating process substrate.

In the substrate processing method in the third aspect, the control unit is configured to control the substrate processing apparatus to perform a procedure including: the fifth step that calculates a warp amount of the process substrate, and the seventh step that determines a supply position from which an organic solvent is to be supplied to a peripheral portion of the coating film, based on the warp amount, and supplies the organic solvent from the supply position to dissolve the peripheral portion of the coating film and remove the same from the rotating process substrate. Since the supply position from which the organic solvent is to be supplied to a peripheral portion of the coating film can be property determined based on the warp amount of the process substrate, the removal width of the peripheral portion can be made more uniform. As a result, even if the process substrate is warped, the periphery of the process substrate can be properly processed. In addition, since circuits can be formed on the surface of the process substrate in areas close to the periphery, higher integration of circuits on the process substrate is achieved whereby the process substrate can be more efficiently utilized.

The substrate processing apparatus in the third aspect may further comprise an irradiating unit configured to irradiate a peripheral portion of the surface of the process substrate with energy beam, wherein the control unit is configured to control the irradiating unit to perform a periphery exposure step that exposes, after the seventh step, the coating film in the peripheral portion of the surface of the process substrate at a predetermined exposure width over the whole periphery of the process substrate, and wherein in the periphery exposure step the exposure width is determined based on the warp amount calculated in the fifth step. In this case, since the exposure width can be properly determined depending on the warp amount of the process substrate, the exposure width of the peripheral portion can be made more uniform. Thus, by developing the process substrate after the peripheral exposure step, the removal width of the peripheral portion can be made more uniform.

The substrate processing apparatus in the third aspect may further comprise a memory unit that stores information on the process substrate, wherein the control unit is configured to control the substrate processing apparatus to perform the procedure further including: an eighth step that heats the coating film after the seventh step; a ninth step that takes, after the eighth step, an image of the end face of the process substrate over the whole periphery of the process substrate by means of said at least one camera; a tenth step that performs image processing of the image taken in the ninth step, thereby to obtain shape data of the end face of the process substrate over the whole periphery of the process substrate; an eleventh step that calculates a warp amount of the process substrate based on the shape data obtained in the second step and the shape data obtained in the tenth step; and a storing step that stores in the memory unit information that the process substrate should not be subjected to an exposure process, if the warp amount calculated in the eleventh step is greater than a threshold value. In this case, a process substrate that is difficult to be exposed by an exposure apparatus can be discriminated beforehand and the process substrate can be excluded from the exposure process. Thus, the process efficiency of process substrates can be improved.

The substrate processing apparatus according to the third aspect may further comprise an irradiating unit configured to irradiate a peripheral portion of the surface of the process substrate with energy beam, wherein the control unit is configured to control the substrate processing apparatus to perform the procedure further including: an eighth step that heats the coating film after the seventh step; a ninth step that takes, after the eighth step, an image of the end face of the process substrate over the whole periphery of the process substrate by means of said at least one camera; a tenth step that performs image processing of the image taken in the ninth step, thereby to obtain shape data of the end face of the process substrate over the whole periphery of the process substrate; an eleventh step that calculates a warp amount of the process substrate based on the shape data obtained in the second step and the shape data obtained in the tenth step; and a periphery exposure step that controls, after the ninth step, the irradiating unit and exposes the coating film in the peripheral portion of the surface of the process substrate at a predetermined exposure width over the whole periphery of the process substrate, and wherein in the periphery exposure step the exposure width is determined based on the warp amount calculated in the fifth step. In this case, since the exposure width can be more properly determined depending on the warp amount of the process substrate that has been subjected to the heating process in the eighth step, the exposure width of the peripheral portion can be made more uniform. Thus, by developing the process substrate after the peripheral exposure step, the removal width of the peripheral portion can be made more uniform.

The substrate processing apparatus according to the third aspect may further comprise a memory unit that stores information on the process substrate, wherein the control unit is configured to control the substrate processing apparatus to perform the procedure further including: a storing step that stores in the memory unit information that the process substrate should not be subjected to an exposure process, if the warp amount calculated in the eleventh step is greater than a threshold value. In this case, a process substrate that is difficult to be exposed by an exposure apparatus can be discriminated beforehand and the process substrate can be excluded from the exposure process. Thus, the process efficiency of process substrates can be improved.

A substrate processing apparatus in a fourth aspect of the present disclosure comprises: a coating liquid supplying unit configured to supply a coating liquid onto a surface of a process substrate; an irradiating unit configured to irradiate a peripheral portion of the surface of the process substrate with energy beam; at least one camera; and a control unit, wherein the control unit is configured to control the substrate processing apparatus to perform a procedure including: a first step that takes an image of an end face of a reference substrate, whose warp amount is known, over a whole periphery of the reference substrate by means of said at least one camera; a second step that performs image processing of the image taken in the first step, thereby to obtain shape data of the end face of the reference substrate over a whole periphery of the reference substrate; a third step that takes an image of an end face of a process substrate over a whole periphery of the process substrate by means of said at least one camera; a fourth step that performs image processing of the image taken in the third step, thereby to obtain shape data of the end face of the process substrate over a whole periphery of the process substrate; a fifth step that calculates a warp amount of the process substrate based on the shape data obtained in the second step and the shape data obtained in the fourth step; a sixth step that controls the coating liquid supplying unit and supplies a coating liquid to a surface of the process substrate thereby to form a coating film on the surface of the process substrate; a periphery exposure step that controls, after the sixth step, the irradiating unit and exposes the coating film in the peripheral portion of the surface of the process substrate at a predetermined exposure width over the whole periphery of the process substrate, and wherein in the periphery exposure step the exposure width is determined based on the warp amount calculated in the fifth step.

In the substrate processing apparatus in the fourth aspect, control unit is configured to control the substrate processing apparatus to perform a procedure including: the fifth step that calculates a warp amount of the process substrate, and the periphery exposure step that determines the exposure width based on the warp amount. Since the exposure width can be property determined based on the warp amount of the process substrate, the exposure width of the peripheral portion can be made more uniform. Thus, by developing the process substrate after the peripheral exposure step, the removal width of the peripheral portion can be made more uniform. As a result, even if the process substrate is warped, the periphery of the process substrate can be properly processed. In addition, since circuits can be formed on the surface of the process substrate at areas close to the periphery, higher integration of circuits on the process substrate is promoted whereby the process substrate can be more efficiently utilized.

The substrate processing apparatus in the fourth aspect may further comprise a heating unit configured to heat the process substrate, wherein the control unit is configured to control the substrate processing apparatus to perform the procedure further including: a seventh step that heats, after the sixth step, the coating unit by means of the heating unit, wherein the third, fourth and fifth steps are performed after the seventh step. In this case, since the exposure width can be more properly determined based on on the warp amount of the process substrate that has been subjected to the heating process in the seventh step, the exposure width of the peripheral portion can be made more uniform. Thus, by developing the process substrate after the periphery exposure step, the removal width of the peripheral portion can be made more uniform.

The substrate processing apparatus in the fourth aspect may further comprise a memory unit that stores information on the process substrate, wherein the control unit is configured to control the substrate processing apparatus to perform the procedure further including: a storing step that stores in the memory unit information that the process substrate should not be subjected to an exposure process, if the warp amount calculated in the fifth step is greater than a threshold value. In this case, a process substrate that is difficult to be exposed by an exposure apparatus can be discriminated beforehand and the process substrate can be excluded from the exposure process. Thus, the process efficiency of process substrates can be improved.

The substrate processing apparatus in the fourth aspect may further comprise a second rotary holding unit configured to hold and rotate the process substrate, wherein the control unit is configured to control the second rotary holding unit to rotate the process substrate in the third step, and wherein during rotation of the process substrate the image of the end face of the process substrate over the whole periphery of the process substrate is taken by means of said at least one camera in the third step, and wherein parts of the first rotary holding unit for holding the process substrate have the same size as parts of the second rotary holding unit for holding the process substrate. When the rotary holding unit holds a process substrate, stresses are induced in parts between the rotary holding unit and the process substrate so that the warp amount of the process substrate may vary. As described above, when the parts of the first rotary holding unit for holding the process substrate have the same size as the parts of the second rotary holding unit for holding the process substrate, stresses induced in the parts between the respective rotary holding units and the process substrate are substantially the same. Thus, variation of the warp amount when the third, fourth and fifth steps calculate the warp amount of a process substrate, and variation of the warp amount when the seventh step that supplies the organic solvent to the peripheral portion of the coating film are substantially the same. Thus, in the seventh step, the supply position from which an organic solvent is to be supplied to the peripheral portion of the coating film can be easily determined.

The substrate processing apparatus in the fourth aspect may further comprise first and second rotary holding unit each configured to hold and rotate the process substrate, wherein the control unit is configured to control the first rotary holding unit to rotate the process substrate in the third step, and wherein during rotation of the process substrate the image of the end face of the process substrate over the whole periphery of the process substrate is taken by means of said at least one camera in the third step, wherein the control unit is configured to control the second rotary holding unit to rotate the process substrate in the periphery exposure step, and wherein during rotation of the process substrate the coating film in the peripheral portion of the surface of the process substrate is exposed at a predetermined exposure width over the whole periphery of the process substrate, and wherein parts of the first rotary holding unit for holding the process substrate have the same size as parts of the second rotary holding unit for holding the process substrate. When the rotary holding unit holds a process substrate, stresses are induced in parts between the rotary holding unit and the process substrate so that the warp amount of the process substrate may vary. As described above, when the parts of the first rotary holding unit for holding the process substrate have the same size as the parts of the second rotary holding unit for holding the process substrate, stresses induced in the parts between the respective rotary holding units and the process substrate are substantially the same. Thus, variation of the warp amount when the third, fourth and fifth steps calculate the warp amount of a process substrate, and variation of the warp amount when the periphery exposure step exposes the peripheral portion of the coating film are substantially the same. Thus, in the periphery exposure step, the exposure width of the peripheral portion of the coating film can be easily determined.

A first processing chamber in which the third step that takes the image of the process substrate is performed, may be different from a second processing chamber in which the tenth step that takes the image of the process substrate is performed.

The substrate processing apparatus in the fourth aspect may further comprise a second rotary holding unit configured to hold and rotate the process substrate; and a mirror member having a reflecting surface that opposes an end face of the substrate and a peripheral portion of a back surface of the substrate held by the second rotary holding unit, the reflecting surface being inclined with respect to a rotation axis of the rotary holding unit; wherein one of said at least one camera has an imaging device that receives both first light and second light through a lens, the first light coming from a peripheral portion of a front surface of the substrate held by the second rotary holding unit, and the second light being a reflected light of second light which comes from the end face of the substrate held by the second rotary holding unit and is reflected by the reflecting surface. In this case, both the peripheral portion of the front surface of the process substrate and the end face of the substrate can be simultaneously imaged by the one camera. Thus, since a plurality of cameras are no longer necessary, a space for installation of these cameras is unneeded. In addition, since a mechanism for moving the camera is unnecessary, a space for installation of the mechanism is unneeded. Therefore, the imaging unit can achieve reduction in size and decrease in cost.

The reference substrate may be flat; the control unit may be configured to control the substrate processing apparatus such that: the second step obtains, as the shape data of the end face of the reference substrate, data on a first profile line passing through a center of the end face of the reference substrate; the fourth step obtains, as the shape data of the end face of the process substrate, data on a second profile line passing through a center of the end face of the process substrate; and the fifth step calculates the warp amount of the process substrate based on the data on the first profile line and the data on the second profile line. In this case, the warp amount of the process substrate can be more easily calculated from the data on the first profile line and the data on the second profile line.

The control unit may be configured to control the substrate processing apparatus to perform the procedure further including: a peripheral portion imaging step that takes an image of a peripheral portion of a surface of the process substrate by means of said at least one camera; and an inspecting step that inspects condition of the end face of the process substrate through image processing of the image taken in the fourth step, and inspects condition of the peripheral portion of the process substrate through image processing of the image taken in the peripheral portion imaging step. In this case, a defect (for example, flaw, crack, scratch, etc.) in the vicinity of the periphery of the process substrate can be detected and the process substrate can be excluded from the various processes. Thus, the process efficiency of process substrates can be improved.

A computer-readable storage medium in the fifth aspect of the present disclosure stores a program that makes a substrate processing apparatus execute the aforementioned substrate processing method. Similarly to the above-described substrate processing method, the computer-readable storage medium according to the other aspect of the present disclosure is capable of making more uniform the removal width of the peripheral portion of the coating film. In this specification, the computer-readable storage medium includes a non-transitory tangible medium (non-transitory computer storage medium) (e.g., various main storage apparatus or an auxiliary storage apparatus), and a propagation signal (transitory computer storage medium) (e.g., data signal that can be provided through a network).

The substrate processing method, the substrate processing apparatus and the computer-readable storage medium according to the above can properly perform process to the periphery of a substrate, even if the substrate is warped.

DETAILED DESCRIPTION OF THE INVENTION

It should be firstly noted that the present invention is not limited to the below-described illustrative embodiments. In the below-described description, the same element or an element having the same function are designated by the same reference symbol, and overlapping description is omitted.

<Substrate Processing System>

Figure 1:
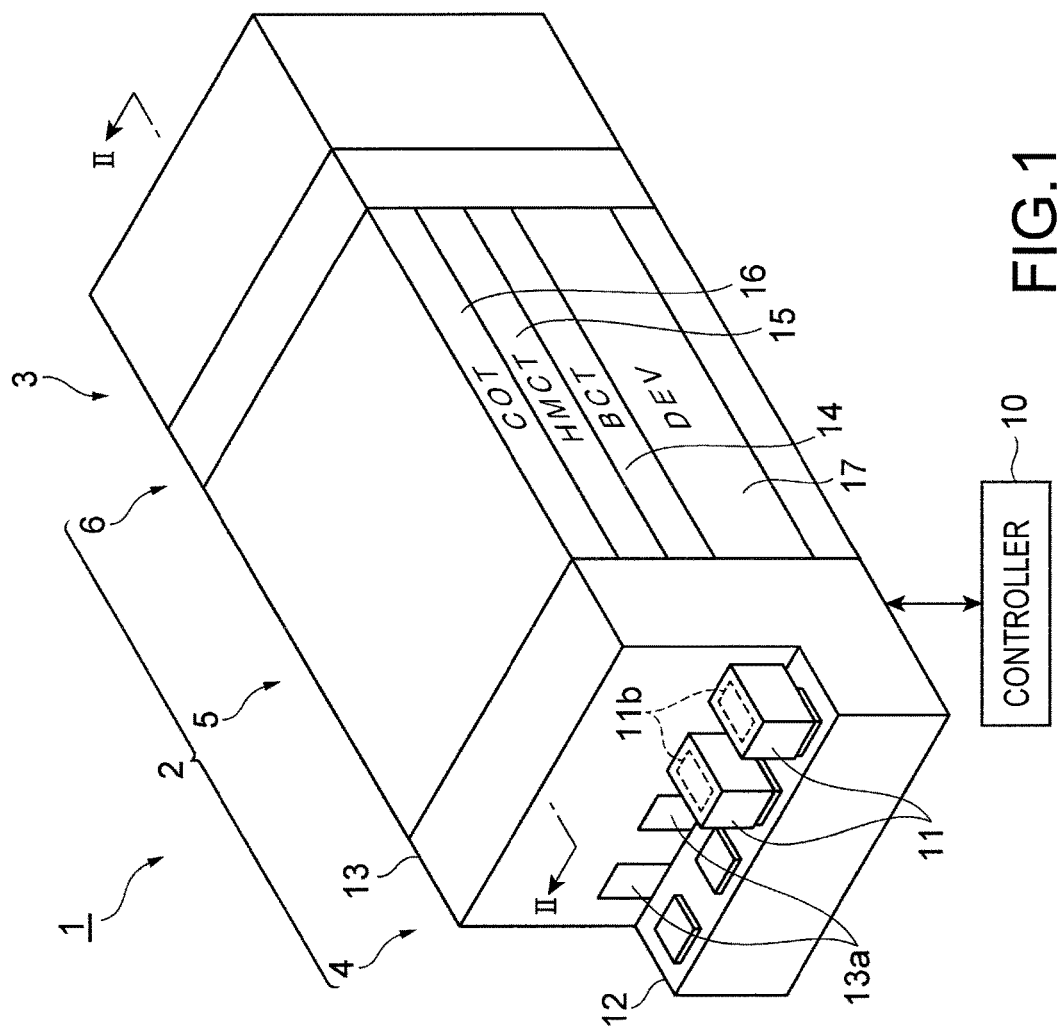
FIG. 1 is a perspective view showing a substrate processing system.

As shown in FIG. 1, a substrate processing system 1 (substrate processing apparatus) includes a coating and developing apparatus 2 (substrate processing apparatus) and a controller 10 (control unit). The substrate processing system 1 is equipped with an exposure apparatus 3. The exposure apparatus 3 has a controller (not shown) capable of communicating with the controller 10 of the substrate processing system 1. The exposure apparatus 3 is configured to send and receive a wafer W (substrate) to and from the coating and developing apparatus 2, and to perform an exposure process (pattern exposure) of a photosensitive resist film formed on a front surface Wa of a wafer W (see FIG. 5). To be specific, a part to be exposed of the photosensitive resist film (photosensitive coating film) is selectively irradiated with an energy ray using a suitable method such as liquid immersion exposure. The energy ray may be, for example, ArF excimer laser, KrF excimer laser, g-ray, i-ray or EUV (Extreme Ultraviolet) ray.

Before the exposure process by the exposure apparatus 3, the coating and developing apparatus 2 performs a process for forming a photosensitive resist film or a non-photosensitive resist film (collectively referred to as "resist film R" herebelow (see FIG. 5)) on the front surface Wa of the wafer W. After the exposure process by the exposure apparatus 3, the coating and developing apparatus 2 performs a process for developing the exposed photosensitive resist film.

The wafer W may have a circular plate shape or may have a plate shape other than the circular shape such as a polygonal shape. The wafer W may have a cutout formed by partially cutting out the wafer W. The cutout may be, for example, a notch (U-shape or V-shaped groove) or a linearly extending part (so-called orientation flat). The wafer W may be, for example, a semiconductor substrate, a glass substrate, a mask substrate, an FPD (Flat Panel Display) substrate, or other various substrates. A diameter of the wafer W may be, for example, about 200 mm to 450 mm. When an edge of the wafer W is beveled (chamfered), the "front surface" in this specification includes the beveled part when seen from the side of the front surface Wa of the wafer W. Similarly, a "back surface" in this specification includes a beveled part when seen from the side of a back surface Wb of the wafer W (see FIG. 5). An "end face" in this specification includes a beveled part when seen from the side of an end face We of the wafer W (see FIG. 5).

As shown in FIGS. 1 to 4, the coating and developing apparatus 2 includes a carrier block 4, a processing block 5 and an interface block 6. The carrier block 4, the processing block 5 and the interface block 6 are horizontally aligned.

Figure 3:
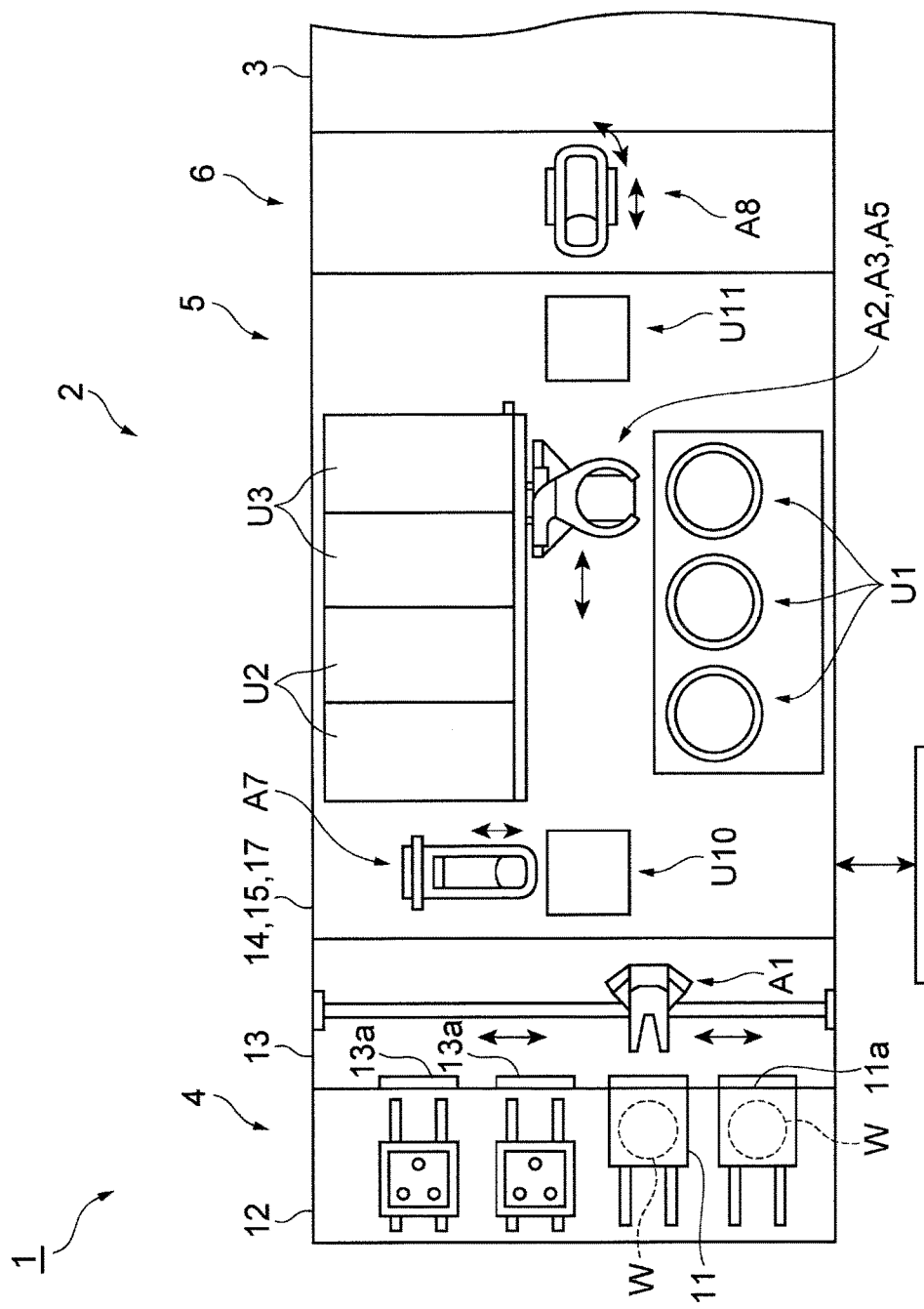
FIG. 3 is a plan view showing unit processing blocks (BCT block, HMCT block, COT block and DEV block).
Figure 4:
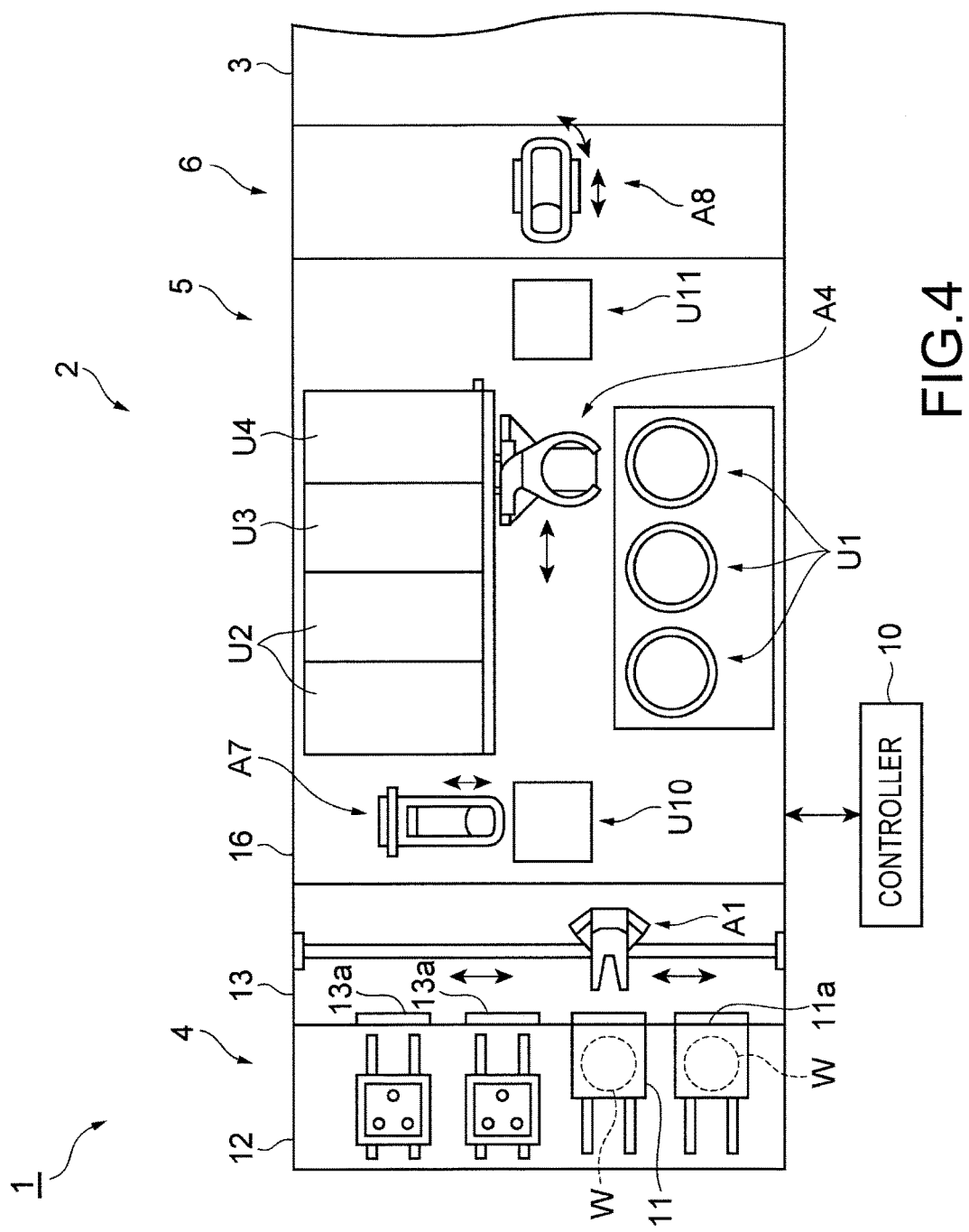
FIG. 4 is a plan view showing the unit processing block (COT block).

As shown in FIGS. 1, 3 and 4, the carrier block 4 includes a carrier station 12 and a loading and unloading unit 13. The carrier station 12 supports thereon a plurality of carriers 11. Each carrier 11 can sealingly contain at least one wafer W. A side surface 11a of the carrier 11 is provided with an opening and closing door (not shown) through which a wafer W is taken into and out from the carrier 11. The carrier 11 is detachably installed on the carrier station 12 such that the side surface 11a faces the loading and unloading unit 13.

A storage medium 11b is disposed in the carrier 11 (see FIG. 1). The storage medium 11b is, for example, a non-volatile memory, and stores information on respective wafers W in the carrier 11 (described later in detail). When the carrier 11 is mounted on the carrier station 12, the controller 10 can access the storage medium 11b, so that information stored in the storage medium 11b can be read out, and that information can be written in the storage medium 11b.

The loading and unloading unit 13 is positioned between the carrier station 12 and the processing block 5. The loading and unloading unit 13 has a plurality of opening and closing doors 13a. When the carrier 11 is placed on the carrier station 12, the opening and closing door of the carrier 11 faces the opening and closing door 13a. By simultaneously opening the opening and closing door 13a and the opening and closing door in the side surface 11a, the inside of the carrier 11 and the inside of the loading and unloading unit 13 communicate with each other. The loading and unloading unit 13 incorporates a delivery arm A1. The deliver arm A1 takes a wafer W out from the carrier 11 and delivers it to the processing block 5, as well as receives a wafer W from the processing block 5 and returns it into the carrier 11.

Figure 2:
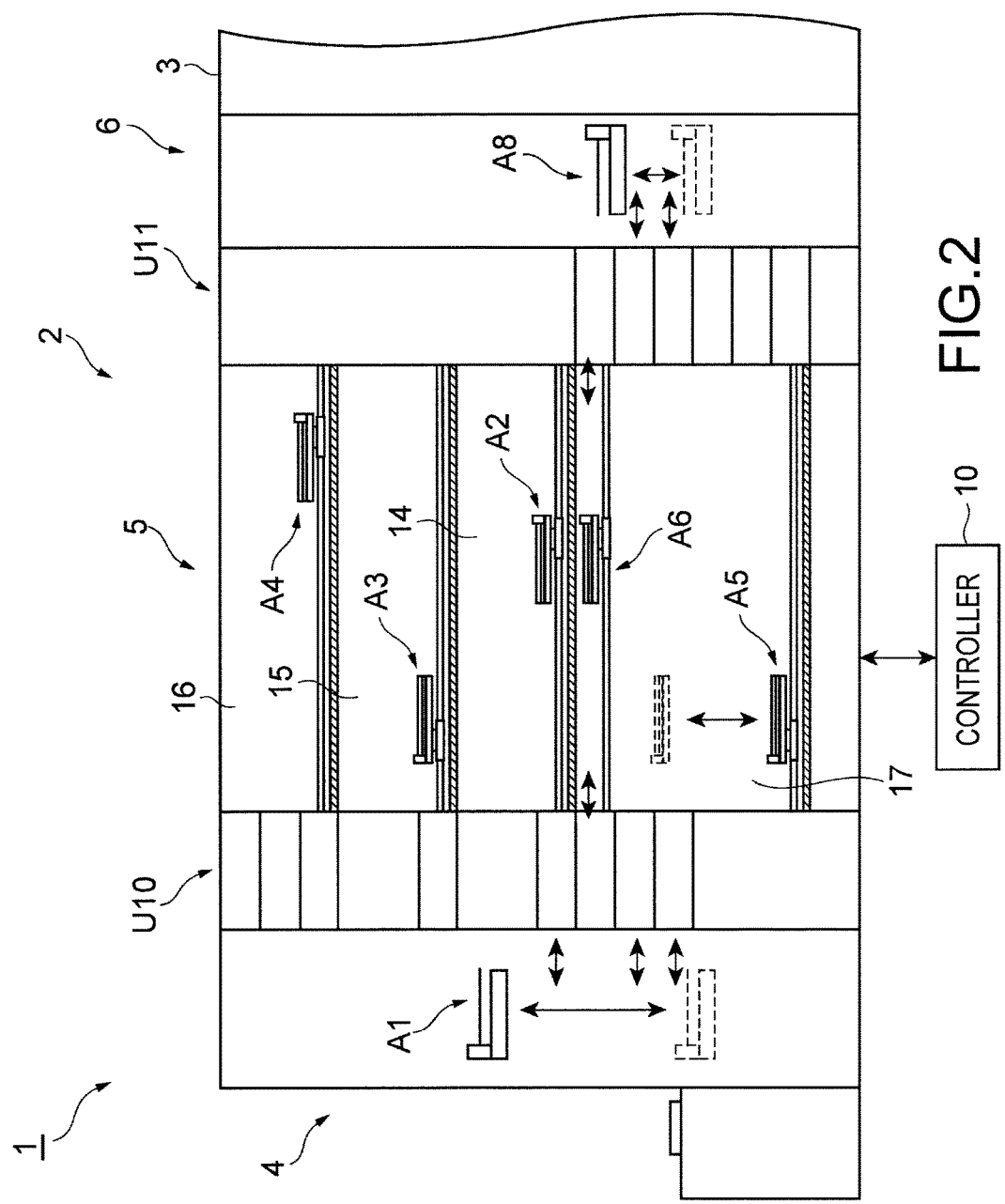
FIG. 2 is a sectional view taken along the II-II line in FIG. 1.

As shown in FIGS. 1 and 2, the processing block 5 has unit processing blocks 14 to 17. The unit processing blocks 14 to 17 are arranged such that the unit processing block 17, the unit processing block 14, the unit processing block 15 and the unit processing block 16 are aligned in this order from the floor surface side. As shown in FIG. 3, each of the unit processing blocks 14, 15 and 17 has a liquid processing unit U1, a thermal processing unit U2 (heating unit) and an inspection unit U3. As shown in FIG. 4, the unit processing block 16 has a liquid processing unit U1, a thermal processing unit U2 (heating unit), an inspection unit U3 and a periphery exposure unit U4.

The liquid processing unit U1 is configured to supply various process liquids to a front surface Wa of a wafer W (described later in detail). The thermal processing unit U2 is configured to perform a thermal process by heating a wafer W by, e.g., a heat plate and cooling the heated wafer W by, e.g., a cooling plate. The inspection unit U3 is configured to inspect respective surfaces (front surface Wa, back surface Wb and end face Wc) of a wafer W (described later in detail). The periphery exposure unit U4 is configured to irradiate a peripheral portion Wd (see FIG. 5) of a wafer W on which a resist film R is formed with ultraviolet ray so as to expose the resist film R on the peripheral portion Wd.

The unit processing block 14 is a lower film forming block (BCT block) configured to form a lower film on a front surface Wa of a wafer W. The unit processing block 14 incorporates a transfer arm A2 that transfers a wafer W to the respective units U1 to U3 (see FIGS. 2 and 3). The liquid processing unit U1 of the unit processing block 14 forms a coating film by coating a front surface Wa of a wafer W with a coating liquid for forming the lower film. The thermal processing unit U2 of the unit processing block 14 performs various thermal processes for forming the lower film. A concrete example of the thermal processes may be a heating process for hardening the coating film into the lower film. The lower film may be an antireflection (SiARC) film, for example.

The unit processing block 15 is an intermediate film (hard mask) forming block (HMCT block) configured to form an intermediate film on the lower film. The unit processing block 15 incorporates a transfer arm A3 that transports a wafer W to the respective units U1 to U3 (see FIGS. 2 and 3). The liquid processing unit U1 of the unit processing block 15 forms a coating film by coating the lower film with a coating liquid for forming the intermediate film. The thermal processing unit U2 of the unit processing block 15 performs various thermal processes for forming the intermediate film. A concrete example of the thermal processes may be a heating process for hardening the coating film into the intermediate film. The intermediate film may be an SOC (Spin On Carbon) film or an amorphous carbon film, for example.

The unit processing block 16 is a resist-film forming block (COT block) configured to form a thermosetting resist film on the intermediate film. The unit processing block 16 incorporates a transfer arm A4 that transfers a wafer W to the respective units U1 to U3 (see FIGS. 2 and 4). The liquid processing unit U1 of the unit processing block 16 forms a coating film by coating the intermediate film with a coating liquid (resist agent) for forming a resist film. The thermal processing unit U2 of the unit processing block 16 performs various thermal processes for forming the resist film. A concrete example of the thermal processes may be a heating process (PAB: Pre Applied Bake) for hardening the coating film into the resist film R.

The unit processing block 17 is a developing block (DEV block) configured to develop the exposed resist film R. The unit processing block 17 incorporates a transfer arm A5 that transfers a wafer W to the respective units U1 to U3, and a direct transfer arm A6 that transfers a wafer W without passing through these units (see FIGS. 2 and 3). The liquid processing unit U1 of the unit processing block 17 develops the exposed resist film R by supplying a developer to the resist film R. The liquid processing unit U1 of the unit processing block 17 supplies a rinse liquid to the developed resist film R so as to rinse away dissolved components of the resist film together with the developer. Thus, the resist film R is partly removed, so that a resist pattern is formed. The thermal processing unit U2 of the unit processing block 17 performs various thermal processes for the developing process. A concrete example of the thermal processes may be a heating process before the developing process (PEB: Post Exposure Bake), a heating process after the developing process (PB: Post Bake) and the like.

As shown in FIGS. 2 to 4, a shelf unit U10 is disposed in the processing block 5 on the side of the carrier block 4. The shelf unit U10 extends from the floor surface to the unit processing block 16, and is divided into a plurality of cells aligned in the vertical direction. An elevation arm A7 is provided near the shelf unit U10. The elevation arm A7 moves a wafer W up and down among the cells of the shelf unit U10.

A shelf unit U11 is disposed in the processing block 5 on the side of the interface block 6. The shelf unit extends from the floor surface to an upper part of the unit processing block 17, and is divided into a plurality of cells aligned in the vertical direction.

The interface block 6 incorporates a delivery arm A8, and is connected to the exposure apparatus 3. The delivery arm A8 is configured to take a wafer W from the shelf unit U11 and deliver it to the exposure apparatus 3, and is configured to receive a wafer W from the exposure apparatus 3 and return it to the shelf unit U11.

The controller 10 controls the substrate processing system 1 partly or entirely. Details of the controller 10 will be described later. The controller 10 can send and receive a signal to and from the controller of the exposure apparatus 3. Due to the cooperation of the respective controllers, the substrate processing system 1 and the exposure apparatus 3 are controlled.

<Structure of Liquid Processing Unit>

Figure 5:
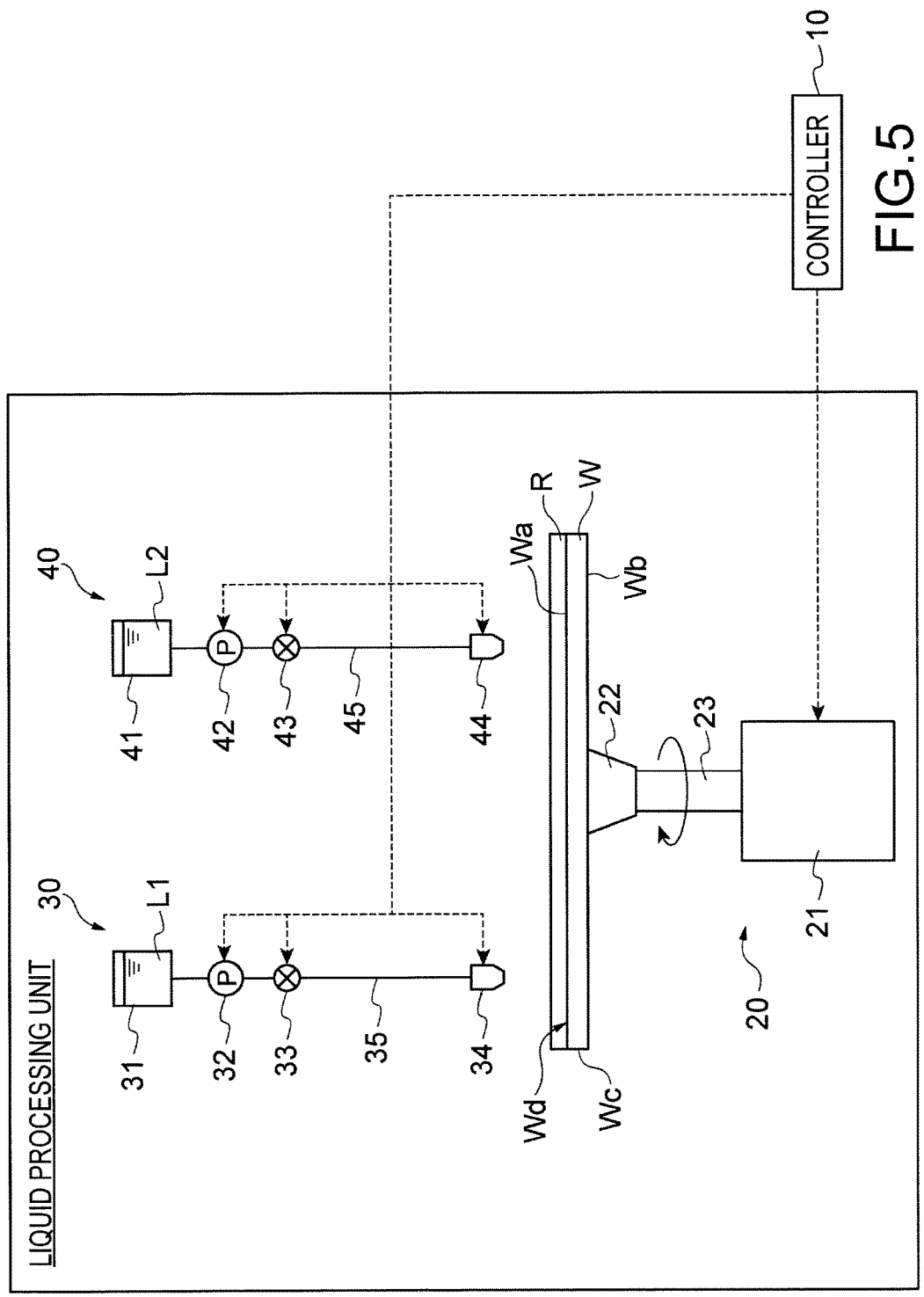
FIG. 5 is a schematic view showing a liquid processing unit.

Next, the liquid processing unit U1 is described in more detail with reference to FIG. 5. As shown in FIG. 5, the liquid processing unit U1 includes a rotary holding unit 20, a liquid supplying unit 30 (coating liquid supplying unit) and a liquid supplying unit 40 (solvent supplying unit).

The rotary holding unit 20 has a rotating unit 21 and a holding unit 22. The rotating unit 21 has a shaft 23 projecting therefrom upward. The rotating unit 21 rotates the shaft 23 by, e.g., an electric motor as a power source. The holding unit 22 is disposed on a distal end of the shaft 23. A wafer W is placed on the holding unit 22. The holding unit 22 is, for example, a suction chuck that substantially horizontally holds a wafer W by suction. The shape of the holding unit 22 (suction chuck) is not specifically limited, and may be circular, for example. The size of the holding unit 22 may be smaller than a wafer W. If the holding unit 22 has a circular shape, the holding unit 22 may have a size of about 80 mm in diameter, for example.

The rotary holding unit 20 rotates the wafer W about an axis (rotation axis) that is perpendicular to a front surface Wa of the wafer W, when the the posture of the wafer W is substantially horizontal. In this embodiment, since the rotation axis passes through the center of the circular wafer W, the rotation axis is also a center axis. In this embodiment, as shown in FIG. 5, the rotary holding unit 20 rotates the wafer W clockwise when seen from above.

The liquid supplying unit 30 is configured to supply a process liquid L1 onto the front surface Wa of the wafer W. In each of the unit processing blocks 14 to 16, the process liquid L1 is a coating liquid for forming a lower film, an intermediate film or a resist film. In this case, the liquid supplying unit 30 functions as a coating liquid supplying unit. In the unit processing block 17, the process liquid is a developer. In this case, the liquid supplying unit 30 functions as a developer supplying unit.

The liquid supplying unit 30 includes a liquid source 31, a pump 32, a valve 33, a nozzle 34 and a pipe 35. The liquid source 31 functions as a supplying source of the process liquid L1. The pump 32 pumps the process liquid L1 from the liquid source 31 into the nozzle 34 through the pipe 35 and the valve 33. The nozzle 34 is disposed above the wafer W such that its discharge port is directed toward the front surface Wa of the wafer W. The nozzle 34 is configured to be movable in the horizontal direction and in the vertical direction by a drive unit, not shown. The nozzle 34 can discharge the process liquid L1 pumped from the pump 32 onto the front surface Wa of the wafer W. The pipe 35 connects the liquid source 31, the pump 32, the valve 33 and the nozzle 34 in this order from the upstream side.

The liquid supplying unit 40 is configured to supply a process liquid L2 onto the front surface Wa of the wafer W. In each of the unit processing blocks 14 to 16, the process liquid L2 is an organic solvent for removing a lower film, an intermediate film or a resist film from the wafer W. In this case, the liquid supplying unit 40 functions as a solvent supplying unit. In the unit processing block 17, the process liquid L2 is a rinse liquid. In this case, the liquid supplying unit 40 functions as a rinse liquid supplying unit.

The liquid supplying unit 40 includes a liquid source 41, a pump 42, a valve 43, a nozzle 44 and a pipe 45. The liquid source 41 functions as a supplying source of the process liquid L2. The pump 42 pumps the process liquid L2 from the liquid source 41 into the nozzle 44 through the pipe 45 and the valve 43. The nozzle 44 is disposed above the wafer W such that its discharge port is directed toward the front surface Wa of the wafer W. The nozzle 44 is configured to be movable in the horizontal direction and in the vertical direction by a drive unit, not shown. The nozzle 44 can discharge the process liquid L2 pumped from the pump 42 onto the front surface Wa of the wafer W. The pipe 45 connects the liquid source 41, the pump 42, the valve 43 and the nozzle 44 in this order from the upstream side.

<Structure of Inspection Unit>

Figure 6:
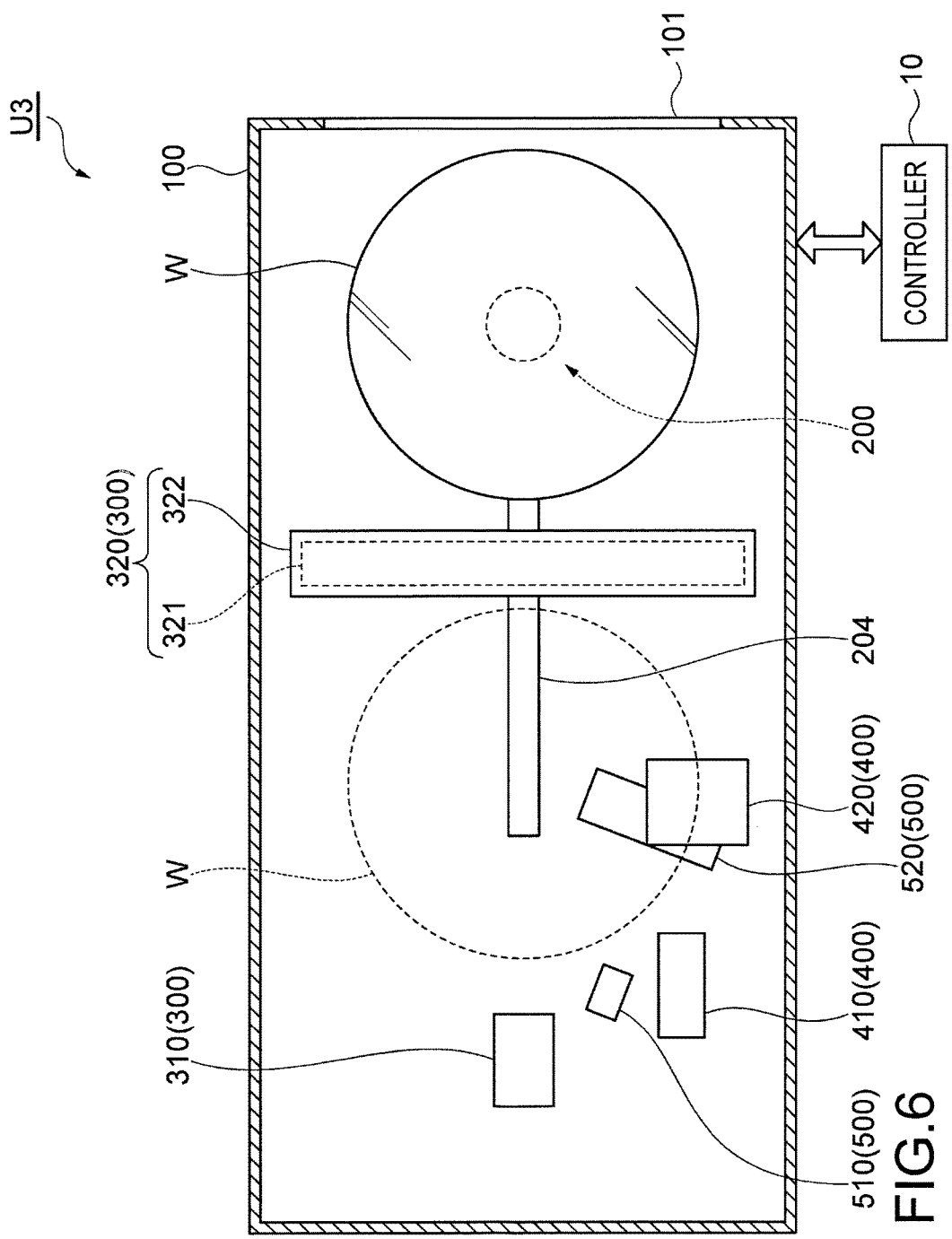
FIG. 6 is a cross sectional view of an inspection unit seen from above.
Figure 7:
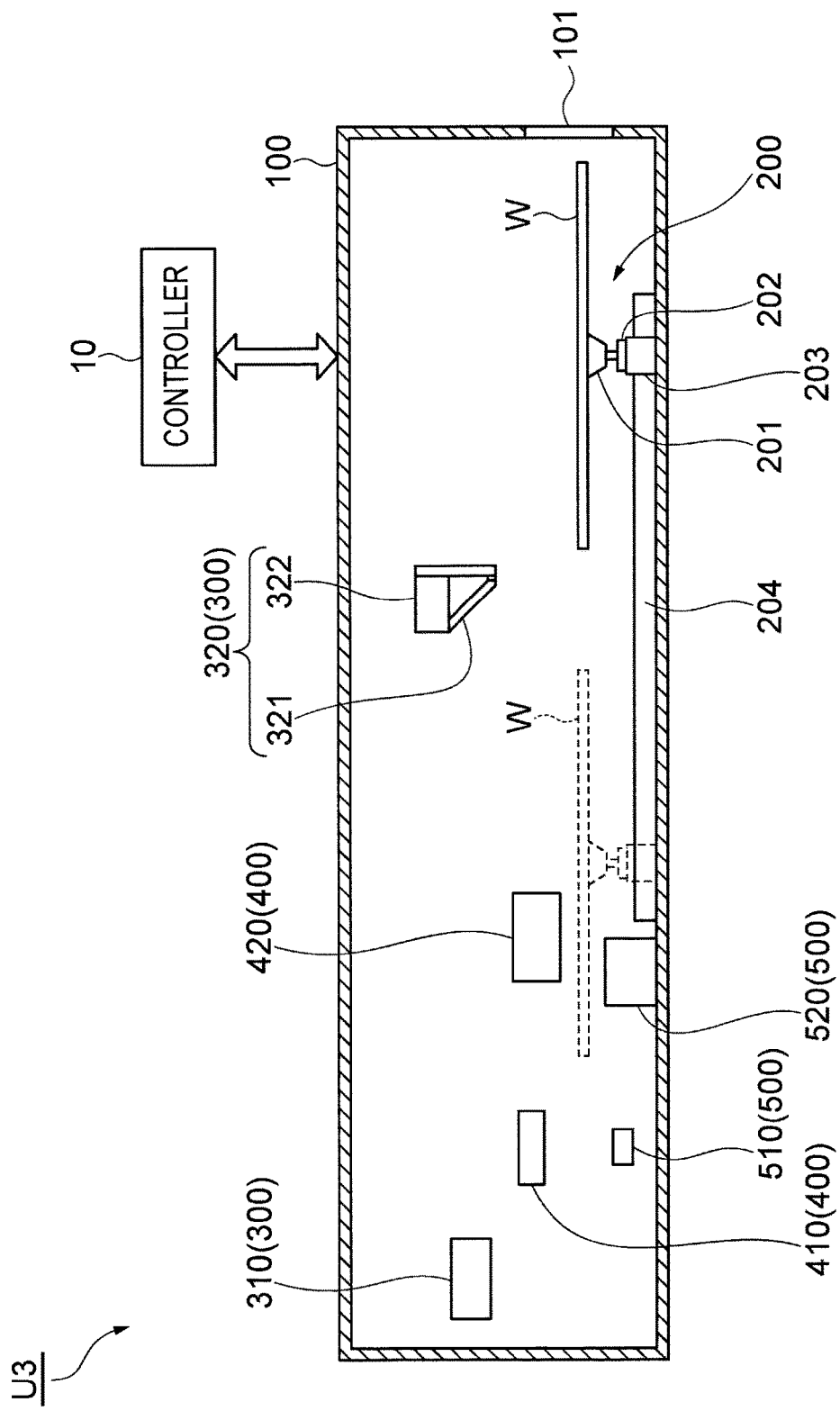
FIG. 7 is a cross sectional view of the inspection unit seen from the lateral side.
Figure 8:
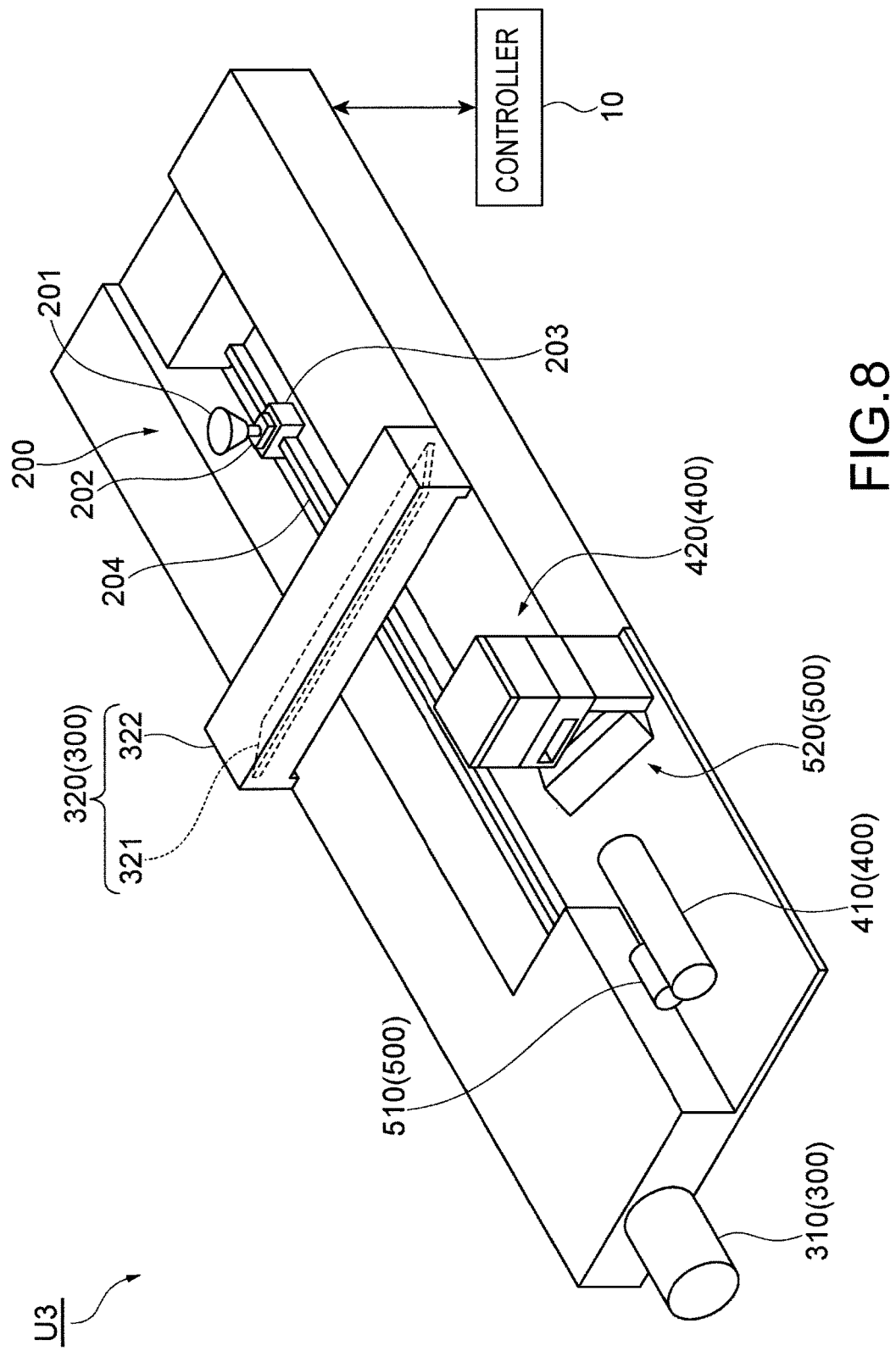
FIG. 8 is a perspective view showing the inspection unit.

Next, the inspection unit U3 is described in more detail with reference to FIGS. 6 to 16. As shown in FIGS. 6 to 8, the inspection unit U3 includes a housing 100, a rotary holding subunit 200 (rotary holding unit), a front surface imaging subunit 300, a periphery imaging subunit 400 (substrate imaging apparatus) and a back surface imaging subunit 500. The respective subunits 200 to 500 are accommodated in the housing 100. A loading and unloading port 101 is formed in one end wall of the housing 100, through which a wafer W is loaded to the inside of the housing 100 and unloaded to the outside of the housing 100.

The rotary holding subunit 200 includes a holding table 201, actuators 202, 203 and a guide rail 204. The holding table 201 is structured as a suction chuck that substantially horizontally holds a wafer W by suction, for example. The shape of the holding table 201 (suction chuck) is not limited, and may be circular, for example. The size of the holding table 201 may be smaller than a wafer W, or may be substantially the same as that of the holding unit 22 (suction chuck). If the holding table 201 has a circular shape, the holding table 201 (suction chuck) may have a size of about 80 mm in diameter, for example.

The actuator 202 is, e.g., an electric motor that drives the holding table 201 in rotation. Namely, the actuator 202 rotates a wafer W held on the holding table 201. The actuator 202 may include an encoder for detecting a rotating position of the holding table 201. In this case, positions of the respective surfaces of a wafer W to be imaged by the respective imaging subunits 300, 400, 500 and the rotating position can be related to each other. If a wafer W has a cutout, the posture of the wafer W can be specified based on the cutout recognized by the respective imaging subunits 300, 400, 500, and the rotating position detected by the encoder.

The actuator 203 is, e.g., a linear actuator that moves the holding table 201 along the guide rail 204. Namely, the actuator 203 allows a wafer W held on the holding table 201 to be transferred between one end and the other end of the guide rail 204. Thus, the wafer W held on the holding table 201 can be moved between a first position near the inlet and outlet port 101, and a second position near the periphery imaging subunit 400 and the back surface imaging subunit 500. The guide rail 204 extends linearly (e.g., like a straight line) in the housing 100.

The front surface imaging subunit 300 includes a camera 310 (imaging means) and an illuminating module 320. The camera 310 and the illuminating module 320 constitute a set of imaging modules. The camera 310 includes a lens and one imaging device (e.g., CCD image sensor, CMOS image sensor, etc.). The camera 310 opposes the illuminating module 320 (illuminating unit).

The illuminating module 320 includes a half mirror 321 and a light source 322. The half mirror 321 is disposed in the housing 100 such that it is inclined at substantially 45° with respect to the horizontal direction. The half mirror 321 is located above an intermediate portion of the guide rail 204 such that the half mirror 321 intersects the guide rail 204 when viewed from above. The half mirror 321 has a rectangular shape. The length of the half mirror 321 is larger than the diameter of a wafer W.

The light source 322 is located above the half mirror 321. The light source 322 is longer than the half mirror 321. Light emitted from the light source 322 passes through the whole half mirror 321 to travel downward (toward the guide rail 204). The light having passed through the half mirror 321 is reflected by an object located below the half mirror 321, and is again reflected by the half mirror 321. The light passes through the lens of the camera 310 and enters the imaging device of the camera 310. Namely, the camera 310 can take an image of an object present in an irradiation area of the light source 322 through the half mirror 321. For example, when the holding table 201 holding a wafer W is moved by the actuator 203 along the guide rail 204, the camera 310 can take an image of the front surface Wa of the wafer W which passes through the irradiation area of the light source 322. Data of the image taken by the camera 310 is transmitted to the controller 10.

As shown in FIGS. 6 to 12, the periphery imaging subunit 400 includes a camera 410 (imaging means), an illuminating module 420 and a mirror member 430. The camera 410, the illuminating module 420 (illuminating unit) and the mirror member 430 constitute a set of imaging modules. The camera 410 includes a lens 411 and one imaging device 412 (e.g., CCD image sensor, CMOS image sensor, etc.). The camera 410 opposes the illuminating module 420.

As shown in FIGS. 9 to 12, the illuminating module 420 is located above the wafer W held on the holding table 201. The illuminating module 420 includes a light source 421, a light scattering member 422 and a holding member 423. The light source 421 may be composed of, for example, a plurality of LED point light sources 421b (see FIG. 12), for example.

Figure 12:
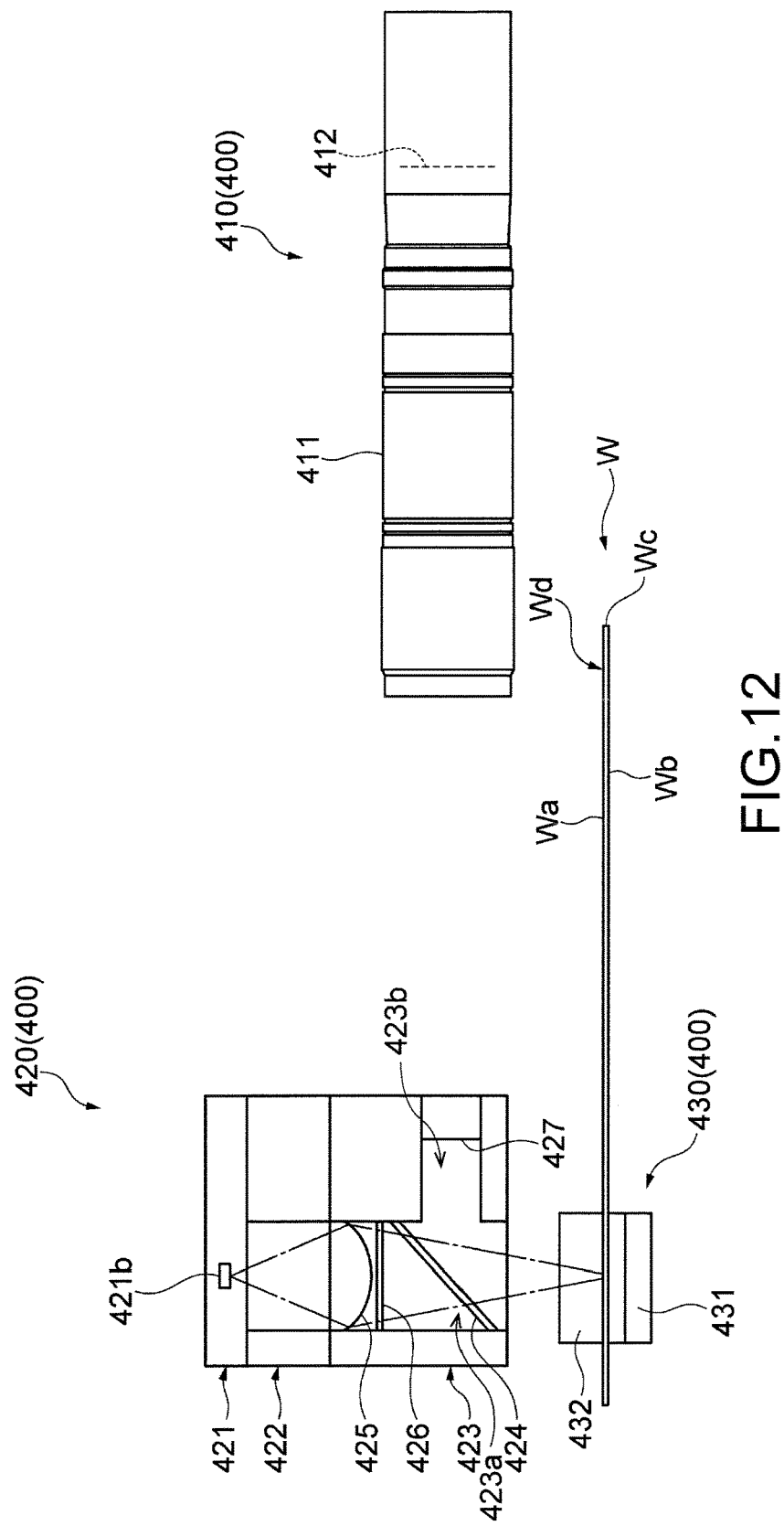
FIG. 12 is a side view of a two-surface imaging module.

As shown in FIGS. 9 to 12, the holding member 423 holds therein a half mirror 424, a cylindrical lens 425, a light diffusing member 426, and focus adjusting lens 427. As shown in FIG. 12, the half mirror 424 is disposed on an intersection part of the through-hole 423a and the intersection hole 423b such that the half mirror 424 is inclined at substantially 45° with respect to the horizontal direction. The half mirror 424 has a rectangular shape.

Figure 9:
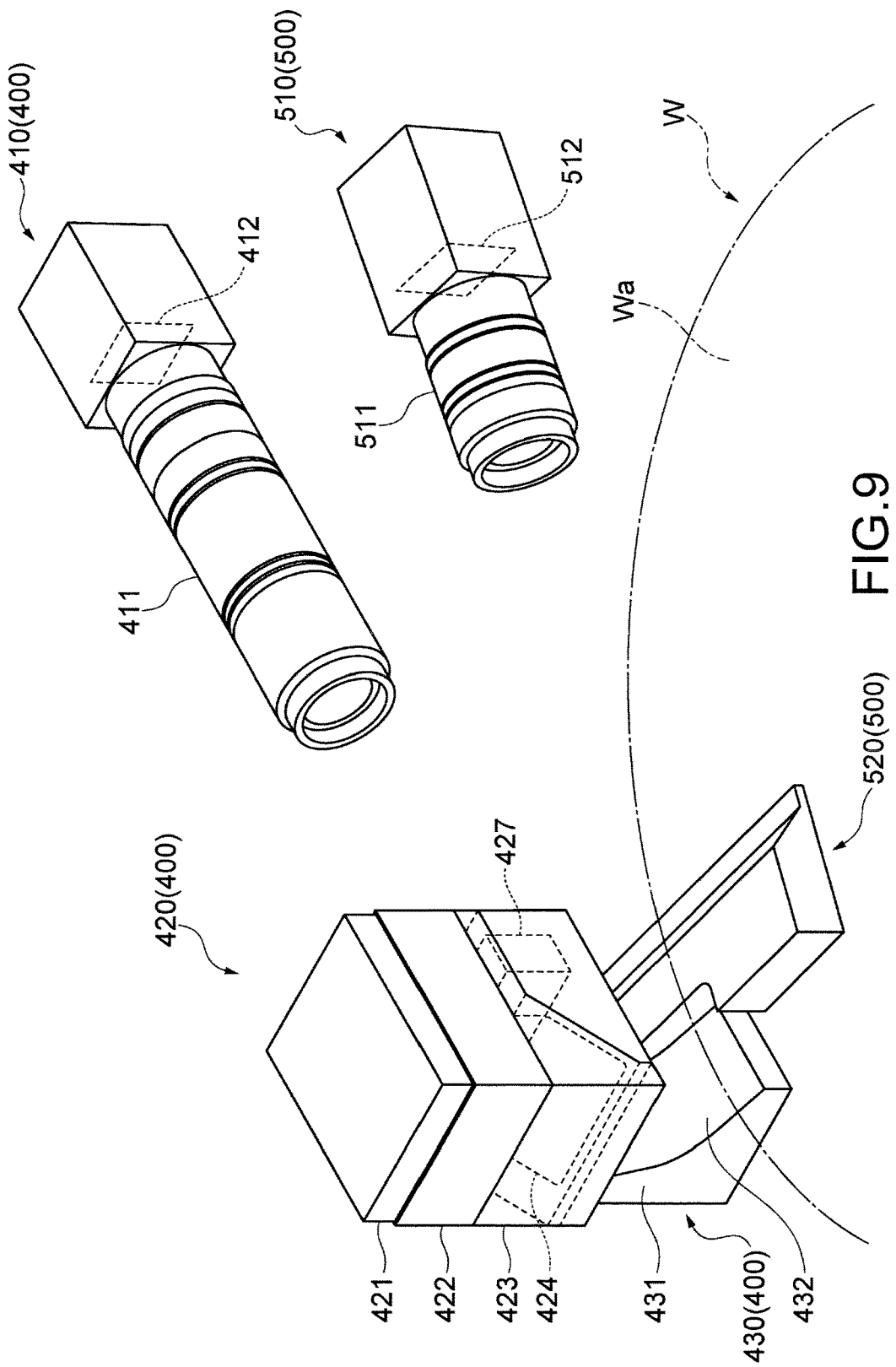
FIG. 9 is a perspective view of a periphery imaging subunit seen from the front side.
Figure 10:
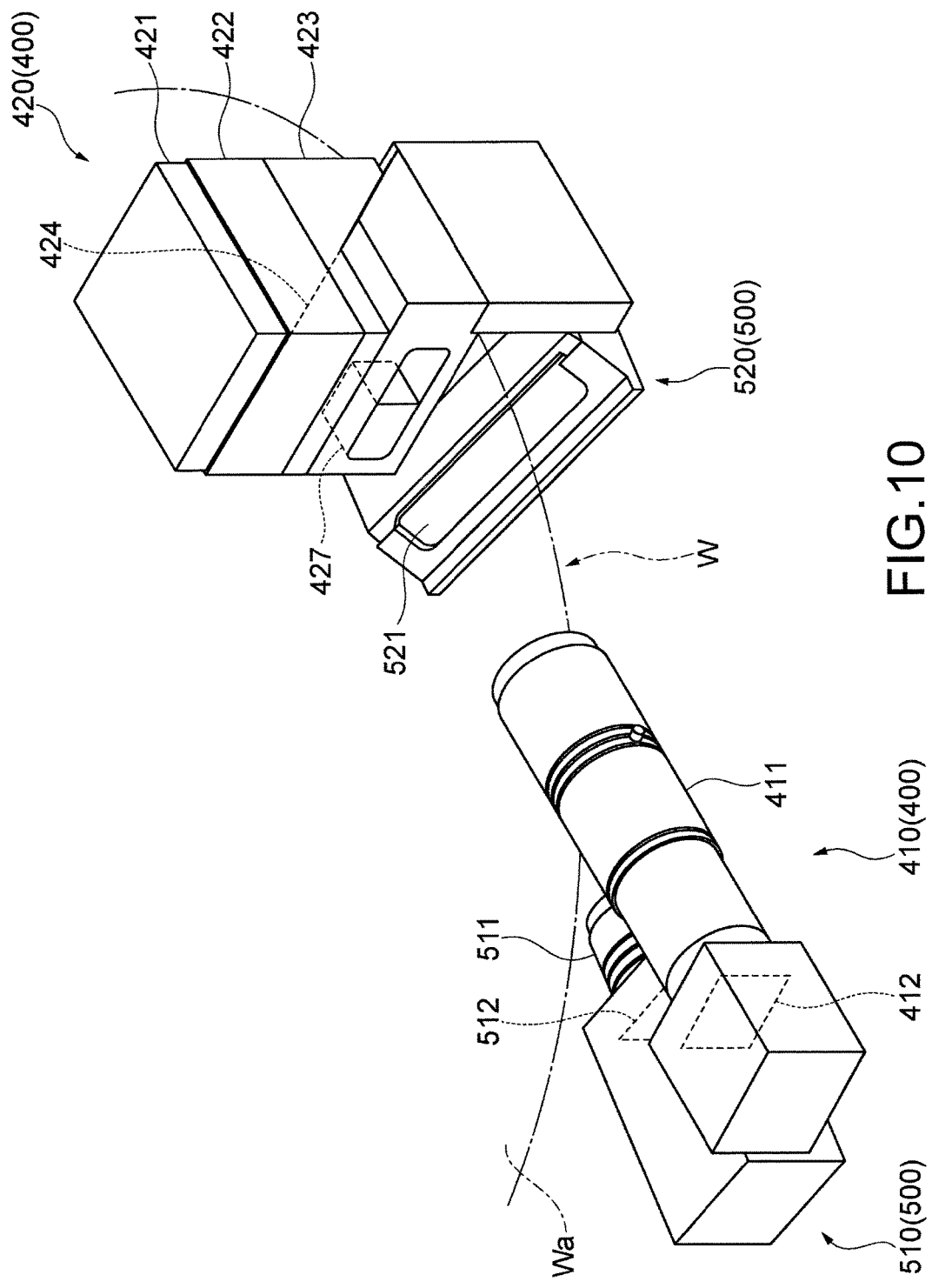
FIG. 10 is a perspective view of the periphery imaging subunit seen from behind.
Figure 11:
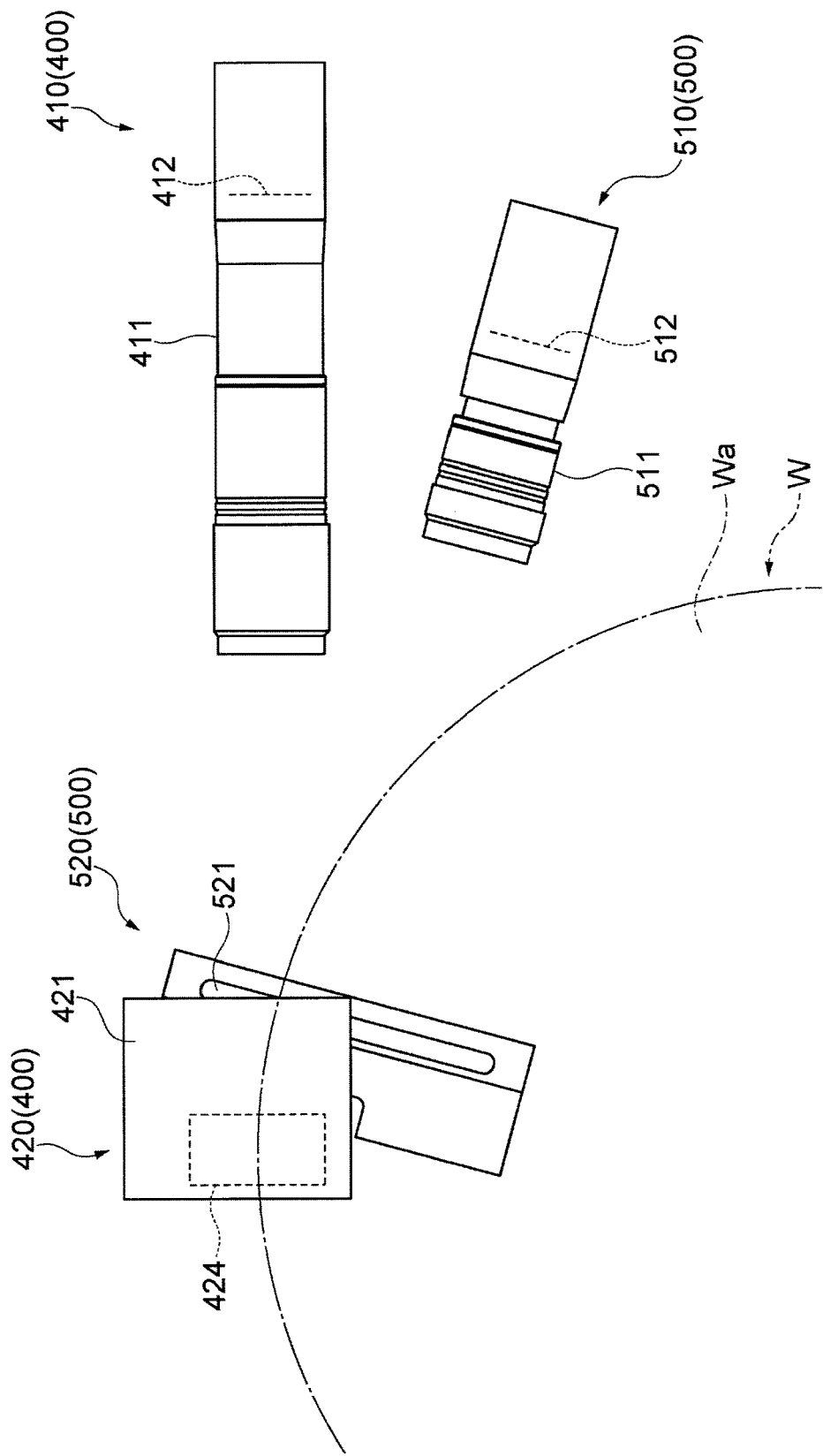
FIG. 11 is a plan view of the periphery imaging subunit.

As shown in FIGS. 9 and 10, the focus adjusting lens 427 is disposed in the intersection hole 423b. As long as the focus adjusting lens 427 is a lens having a function for varying a synthetic focal length with respect to the lens 411, the configuration of the focus adjusting lens 427 is not limited. The focus adjusting lens 427 may be a lens having a parallelepiped shape, for example.

As shown in FIGS. 9 and 12, the mirror member 430 is disposed below the illuminating module 420. As shown in FIGS. 9 and 12 to 14, the mirror member 430 includes a body 431 and a reflecting surface 432. The body 431 is made of an aluminum block.

Figure 14:
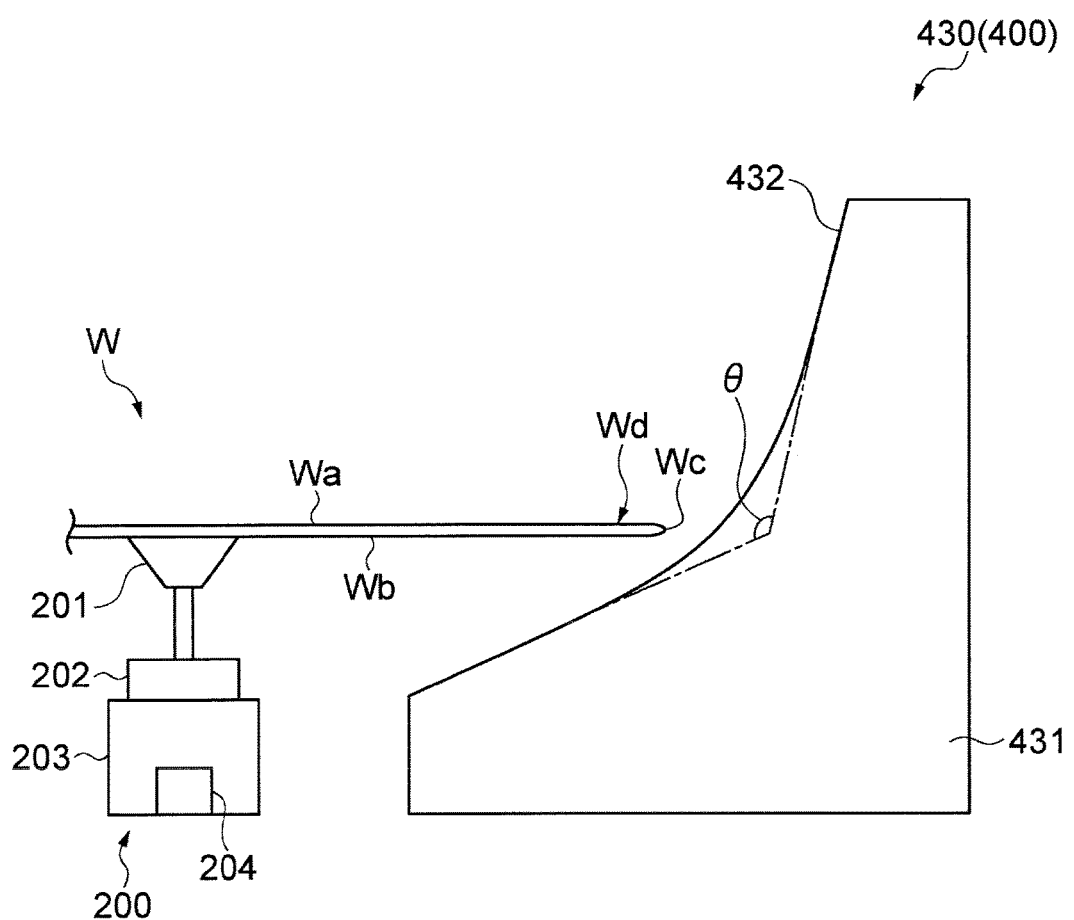
FIG. 14 is a side view showing the mirror member.

As shown in FIGS. 9 and 14, when a wafer W held by the holding table 201 is located at the second position, the reflecting surface 432 opposes an end face Wc of the wafer W and a peripheral portion Wd of a back surface Wb of the wafer W. The reflecting surface 432 is inclined with respect to the rotary axis of the holding table 201. The reflecting surface 432 is mirror finished. For example, a mirror sheet may be attached to the reflecting surface 432. Alternatively, an aluminum plating may be provided to the reflecting surface 432, or an aluminum material may be vapor-deposited on the reflecting surface 432.

The reflecting surface 432 is a curved surface that is recessed away from the end face Wc of the wafer W held on the holding table 201. Namely, the mirror member 430 is a concave mirror. Thus, a mirror image of the end face Wc of the wafer W reflected on the reflecting surface 432 is enlarged. A radius of curvature of the reflecting surface 432 may be about 10 mm to 30 mm, for example. A divergence angle θ (see FIG. 14) of the reflecting surface 432 may be about 100° to 150°. The divergence angle θ of the reflecting surface 432 herein means an angle defined by two planes circumscribing the reflecting surface 432.

Figure 13:
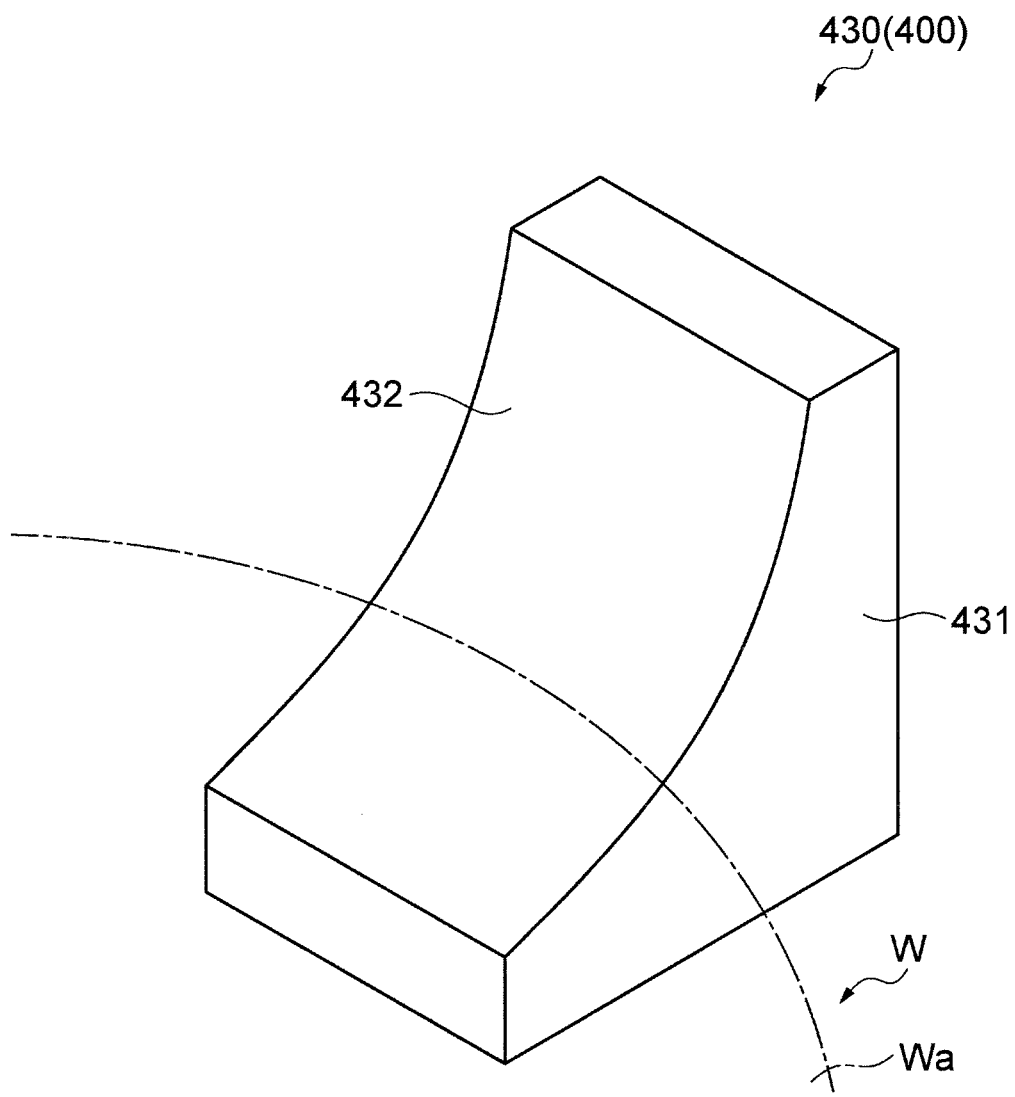
FIG. 13 is a perspective view showing a mirror member.
Figure 15A:
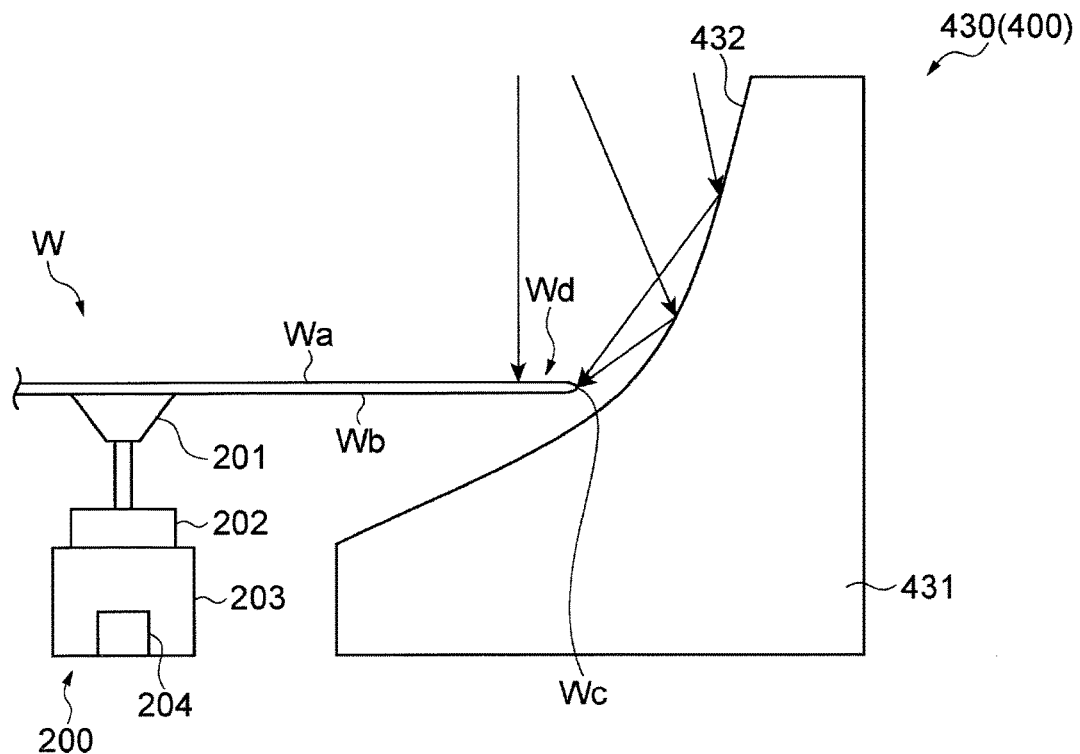
FIG. 15A is a diagram for explaining a condition where light from an illuminating module is reflected by the mirror member.

In the illuminating module 420, light emitted from the light source 421 is scattered by the light scattering member 422, enlarged by the cylindrical lens 425, and diffused by the light diffusing member 426. Thereafter, the light passes through the whole half mirror 424 to travel downward. The diffused light having passed through the half mirror 424 is reflected by the reflecting surface 432 of the mirror member 430 located below the half mirror 424. When a wafer W held on the holding table 201 is located at the second position as shown in FIGS. 13 and 15A, the diffused light having been reflected by the reflecting surface 432 mainly reaches the end face Wc of the wafer W (if the periphery of the wafer W has a beveled part, particularly an upper end of the beveled part) and the peripheral portion Wd of the front surface Wa.

Figure 15B:
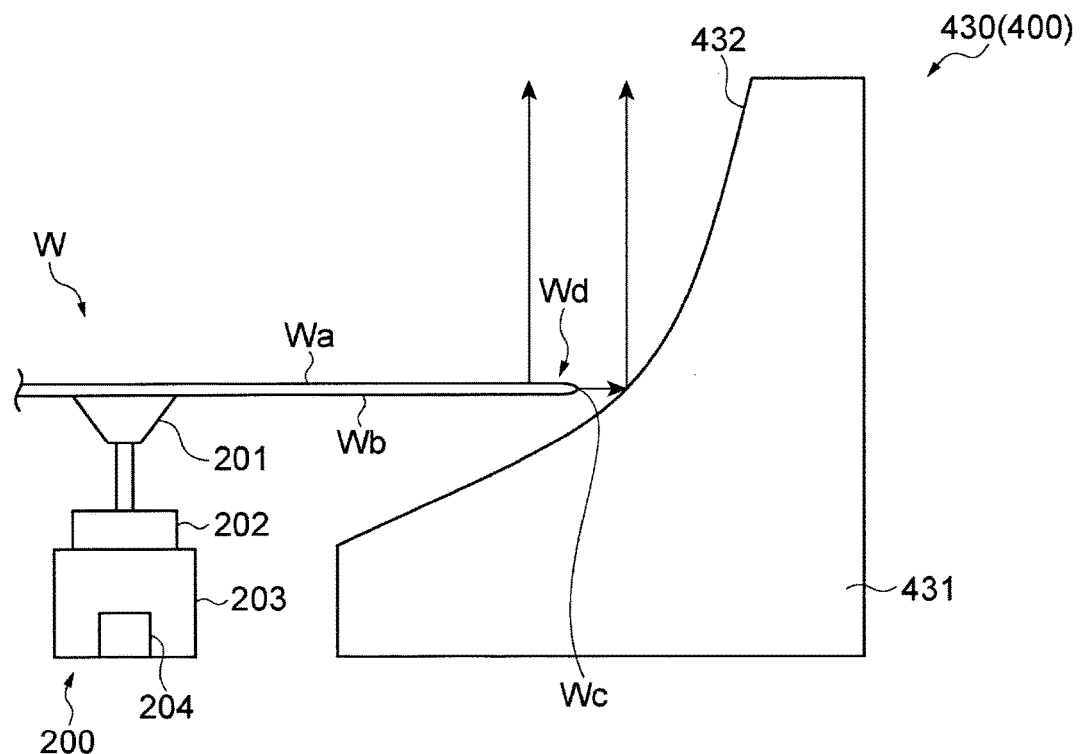
FIG. 15B is a diagram for explaining a condition where light from a wafer is reflected by the mirror member.

The light having been reflected from the peripheral portion Wd of the front surface Wa of the wafer W is not directed toward the reflecting surface 432 of the mirror member 430 but is reflected again by the half mirror 424 (see FIG. 15B). The light then passes through the lens 411 of the camera 410 to enter the imaging device 412 of the camera 410, without passing through the focus adjusting lens 427. On the other hand, the light having been reflected from the end face Wc of the wafer W is reflected sequentially by the reflecting surface 432 of the mirror member 430 and the half mirror 424. The light then passes sequentially through the focus adjusting lens 427 and the lens 411 of the camera 410 to enter the imaging device 412 of the camera 410. Thus, the optical path length of the light coming from the end face Wc of the wafer W to fall on the imaging device 412 of the camera 410 is longer than the optical path length of the light coming from the peripheral portion Wd of the front surface Wa of the wafer W to fall on the imaging device 412 of the camera 410. The optical path difference between these optical paths may be about 1 mm to 10 mm, for example. Thus, the imaging device 412 of the camera 410 receives both the light which comes from the peripheral portion Wd of the front surface Wa of the wafer W and the light which comes from the end face Wc of the wafer W. Namely, when the wafer W held by the holding table 201 is located at the second position, the camera 410 can image both the peripheral portion Wd of the front surface Wa of the wafer W and the end face Wc of the wafer W. Data of the images taken by the camera 410 are transmitted to the controller 10.

If the peripheral portion Wd of the front surface Wa of the wafer W is focused without the existence of the focus adjusting lens 427, the image of the peripheral portion Wd of the front surface Wa of the wafer W taken by the camera 410 is clear, but the image of the end face Wc of the wafer W taken by the camera 410 is likely to be unclear, because of the optical path difference. On the other hand, if the end face of the wafer W is focused without the existence of the focus adjusting lens 427, the image of the end face Wc of the wafer W is clear, but the image of the peripheral portion Wd of the front surface Wa of the wafer W taken by the camera 410 is likely to be unclear, because of the optical path difference. However, since there actually exists the focus adjusting lens 427 in the optical path of the light extending from the reflecting surface 432 of the mirror member 430 to the lens 411, an image forming position, at which an image of the end face Wc of the wafer W is formed, can be adjusted onto the imaging device 412, even though there is the optical path difference. Thus, both the images of the peripheral portion Wd of the front surface Wa of the wafer W and the end face Wc of the wafer W, which were imaged by the camera 410, are clear.

As shown in FIGS. 6 to 11 and 16, the back surface imaging subunit 500 includes a camera 510 (imaging means) and an illuminating module 520 (illuminating unit). The camera 510 and the illuminating module 520 constitute a set of imaging modules. The camera 510 includes a lens 511 and one imaging device 512 (e.g., CCD image sensor, CMOS image sensor, etc.). The camera 510 opposes the illuminating module 520 (illuminating unit).

Figure 16:
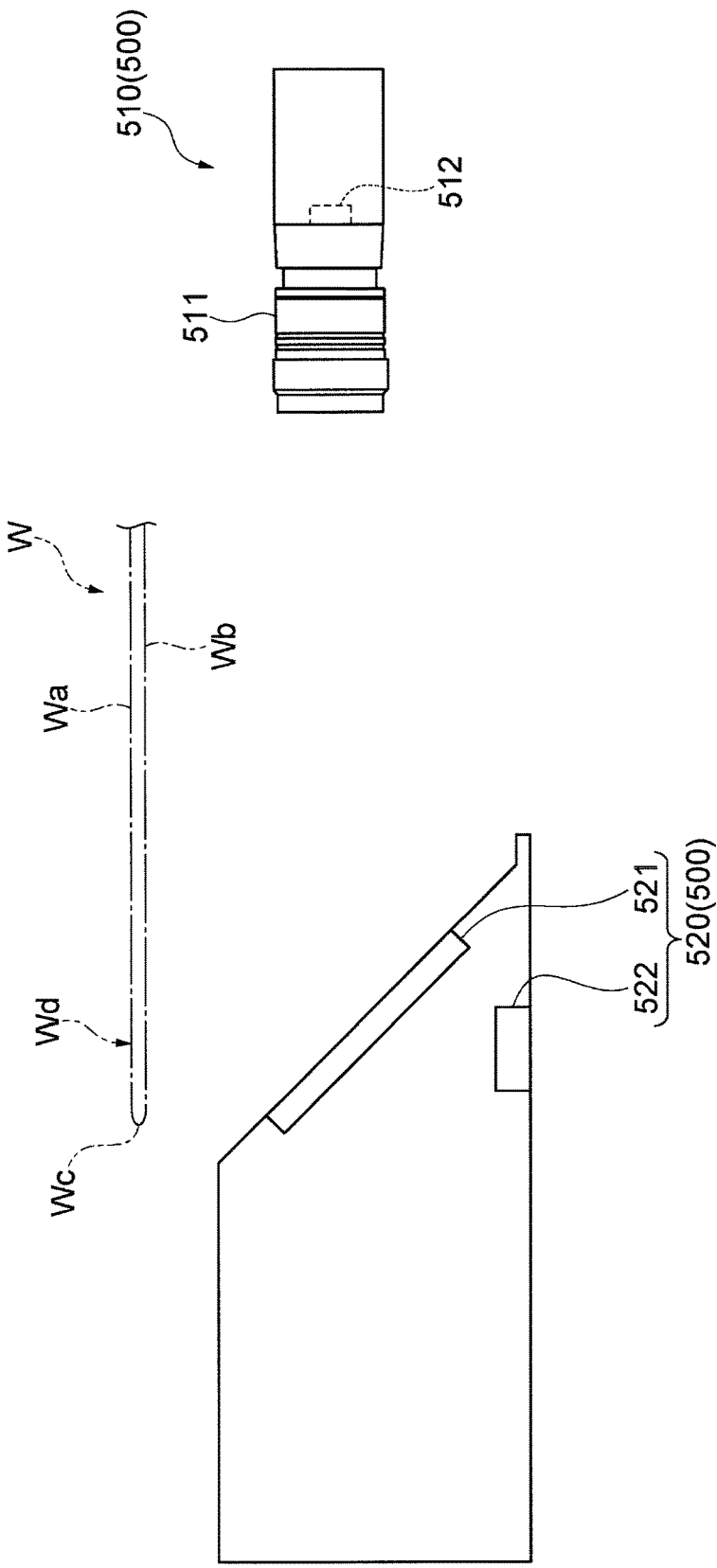
FIG. 16 is a side view of a back-surface imaging subunit.

The illuminating module 520 is located below the illuminating module 420, and below the wafer W held by the holding table 201. As shown in FIG. 16, the illuminating module 520 includes a half mirror 521 and a light source 522. The half mirror 521 is inclined at substantially 45° with respect to the horizontal direction. The half mirror 521 has a rectangular shape.

The light source 522 is located below the half mirror 521. The light source 522 is longer than the half mirror 521. Light emitted from the light source 522 passes through the whole half mirror 521 to travel upward. The light having passed through the half mirror 521 is reflected by an object located above the half mirror 521, and is again reflected by the half mirror 521. Then, the light passes through the lens 511 of the camera 510 to enter the imaging device 512 of the camera 510. Namely, the camera 510 can image an object present in an irradiation area of the light source 522 through the half mirror 521. For example, when the wafer W held by the holding table 201 is located at the second position, the camera 510 can image the back surface Wb of the wafer W. Data of the image imaged by the camera 510 are transmitted to the controller 10.

<Structure of Periphery Exposure Unit>

Figure 17:
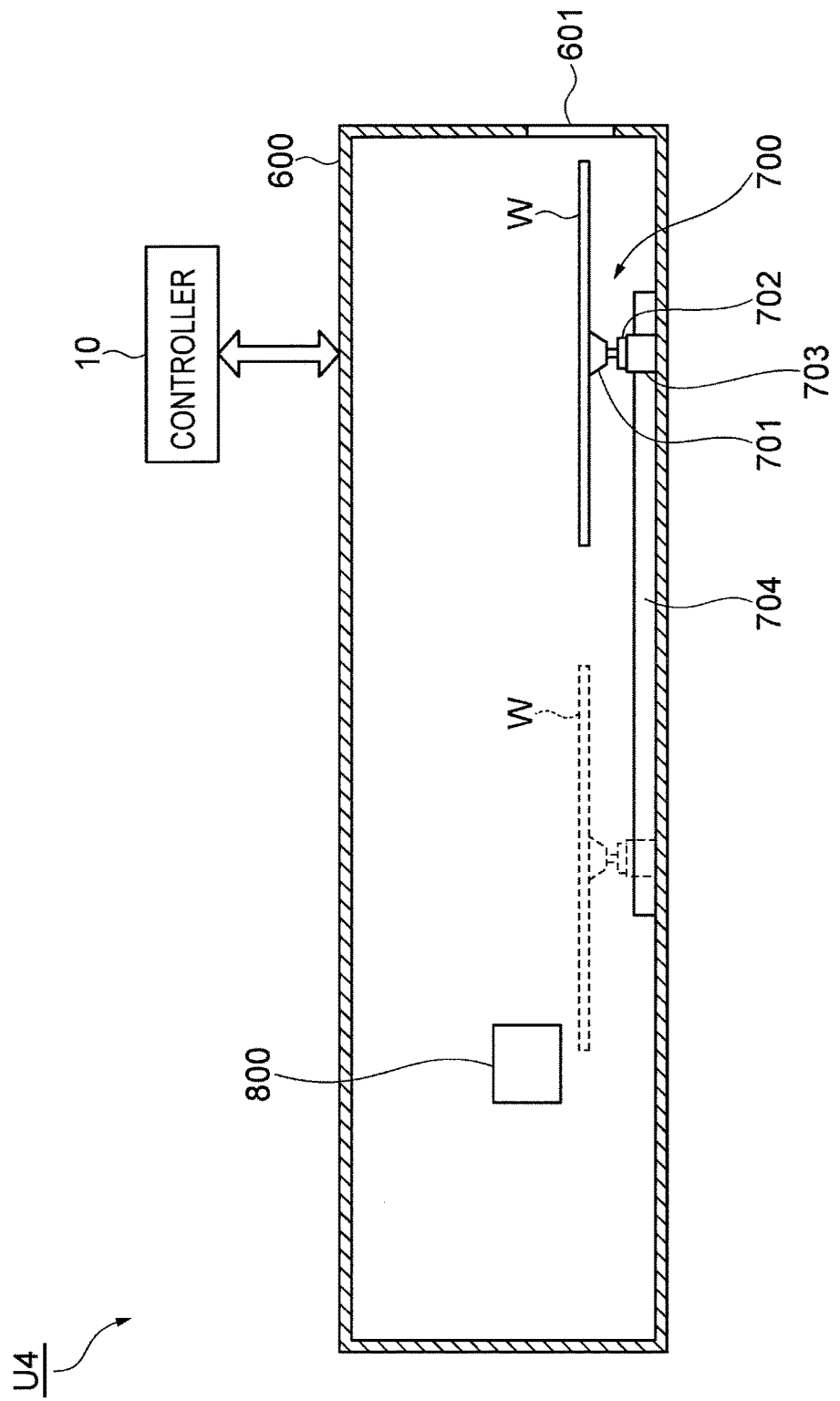
FIG. 17 is a cross sectional view of a periphery exposure unit seen from the lateral side.

Next, the periphery exposure unit U4 is described in more detail with reference to FIGS. 17 and 18. As shown in FIG. 17, the periphery exposure unit U4 includes a housing 600, a rotary holding subunit 700 (rotary holding unit) and an exposure subunit 800 (irradiating unit). The subunits 700 and 800 are disposed in the housing 600. A loading and unloading port 601 is formed in one end wall of the housing 600, through which a wafer W is loaded to the inside of the housing 600 and unloaded to the outside of the housing 600.

Figure 18:
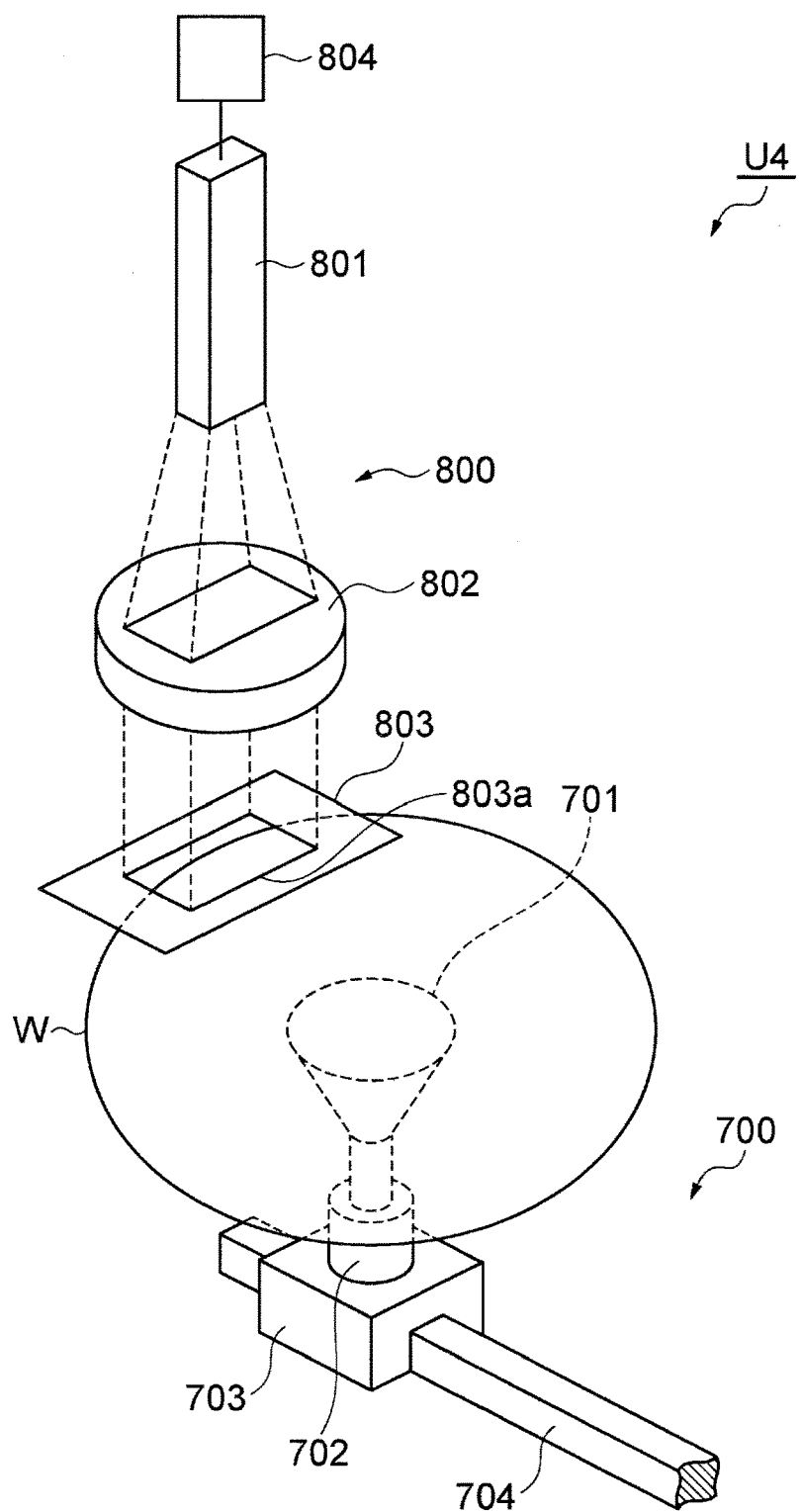
FIG. 18 is a perspective view showing the periphery exposure unit.

As shown in FIGS. 17 and 18, the rotary holding subunit 700 includes a holding table 701, actuators 702, 703 and a guide rail 704. The holding table 701 is structured as a suction chuck that substantially horizontally holds a wafer W by suction, for example. The shape of the holding table 701 (suction chuck) is not limited, and may be circular, for example. The size of the holding table 701 may be smaller than the wafer W, and may be substantially the same as those of the holding unit 22 (suction chuck) and the holding table 201 (suction chuck). If the holding table 701 has a circular shape, the holding table 701 (suction chuck) may have a size of about 80 mm in diameter, for example.

The actuator 702 is, e.g., an electric motor that drives the holding table 701 in rotation. Namely, the actuator 702 rotates the wafer W held on the holding table 701. The actuator 702 may include an encoder for detecting a rotating position of the holding table 701. In this case, the exposure position of a peripheral portion Wd of the wafer W to be exposed by the exposure subunit 800 and the rotating position can be related to each other.

The actuator 203 is, e.g., a linear actuator that moves the holding table 701 along the guide rail 704. Namely, the actuator 703 allows the wafer W held on the holding table 701 to be transferred between one end and the other end of the guide rail 704. Thus, the wafer W held on the holding table 701 can be moved between a first position near the inlet and outlet port 601, and a second position near the exposure subunit 800. The guide rail 704 extends linearly (e.g., like a straight line) in the housing 600.

The exposure subunit 800 is located above the rotary holding subunit 700. As shown in FIG. 18, the exposure subunit 800 includes a light source 801, an optical system 802, a mask 803 and an actuator 804. The light source 801 emits downward (toward the holding table 701) energy beam (e.g., ultraviolet ray) having a wavelength component capable of exposing a resist film R. As the light source 801, an ultrahigh pressure UV lamp, a high pressure UV lamp, a low pressure UV lamp, an excimer lamp and so on may be used.

The optical system 802 is located below the light source 801. The optical system 802 is formed of at least one lens. The optical system 802 converts the light from the light source 801 into a substantially parallel light, which light then reaches the mask 803. The mask 803 is located below the optical system 802. The mask 803 has an opening 803a by which an exposure area is adjusted. The parallel light from the optical system 802 passes through the opening 803a to reach a peripheral portion Wd of a front surface Wa of the wafer W held by the holding table 701.

The actuator 804 is connected to the light source 801. The actuator 804 is, e.g., an elevation cylinder that moves the light source 801 upward and downward. Namely, the light source 801 can be moved by the actuator 804 between a first height position (lowered position) near the wafer W held by the holding table 701, and a second height position (elevated position) remote from the wafer W held by the holding table 701.

<Structure of Controller>

Figure 19:
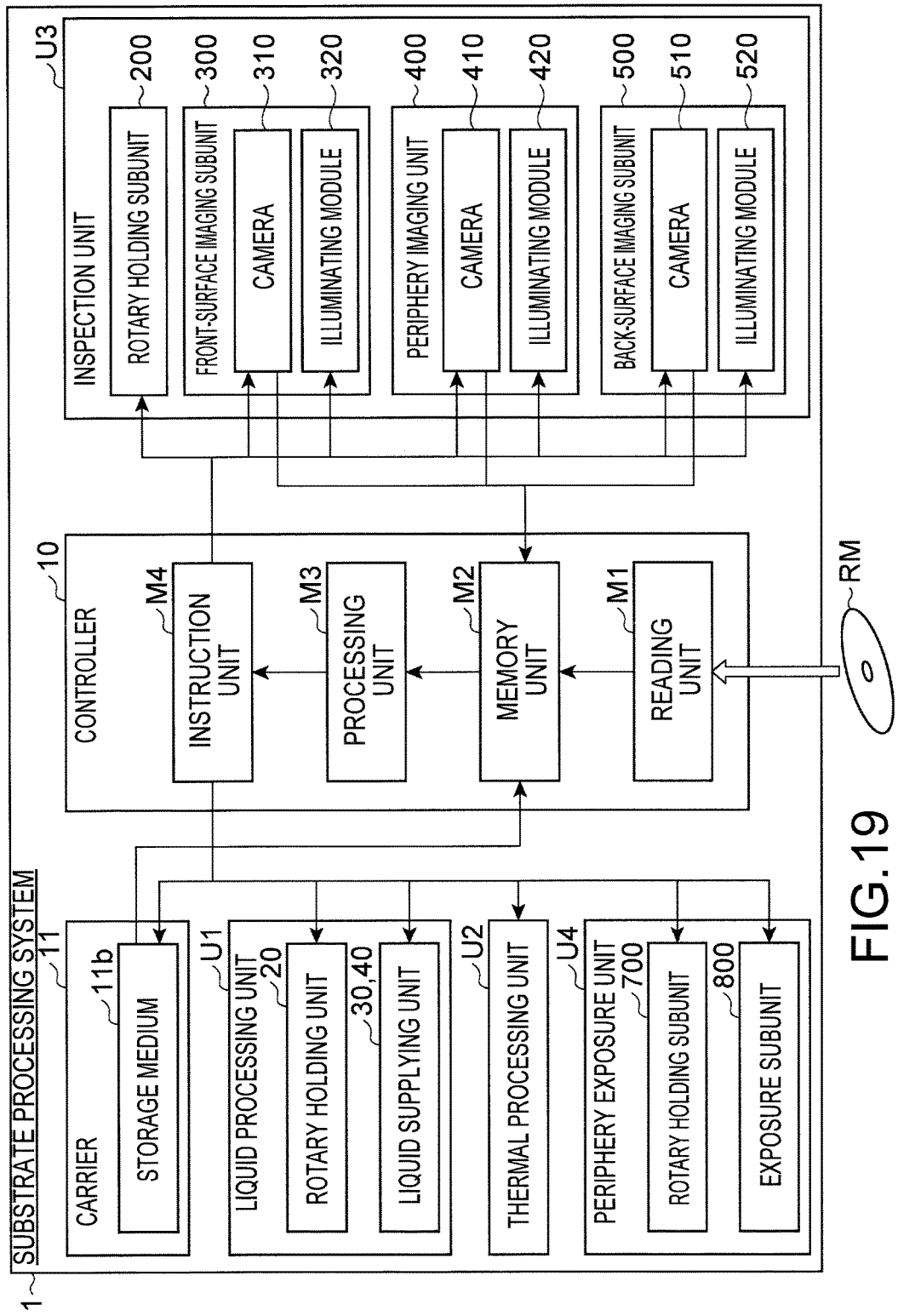
FIG. 19 is a block diagram showing a main part of the substrate processing system.

As shown in FIG. 19, the controller 10 includes, as functional modules, a reading unit M1, a storage unit M2, a processing unit M3 and an instruction unit M4. These functional modules merely correspond to the functions of the controller 10 for the sake of conveniences, and do not necessarily mean that a hardware constituting the controller 10 is divided into these modules. The respective functional modules are not limited to modules whose functions are realized by executing a program, but may be modules whose functions are realized by a dedicated electric circuit (e.g., logic circuit) or an integrated circuit (ASIC: Application Specific Integrated Circuit).

The reading unit M1 reads out a program from a computer-readable recording medium RM. The recording medium RM stores a program for operating respective units of the substrate processing system 1. The recording medium RM may be, for example, a semiconductor memory, an optical memory disc, a magnetic memory disc, or a magneto optic memory disc.

The storage unit M2 stores various data. The storage medium M2 stores various data when the process liquids L1, L2 are supplied to a wafer W (so-called process recipes), set data inputted by an operator through an external input apparatus (not shown) and so on, in addition to a program read out by the reading unit M1 from the recording medium RM, information on a wafer W read out from the storage medium 11b and data of images taken by the cameras 310, 410, 510.

The processing unit M3 processes various data. For example, the processing unit M3 generates, based on various data stored in the storage unit M2, signals for operating the liquid processing unit U1 (for example, rotary holding unit 20, liquid supplying units 30, 40), the thermal processing unit U2, the inspection unit U3 (for example, the rotary holding subunit 200, cameras 310, 410, 510, illuminating modules 320, 420, 520) and the periphery exposure unit U4 (for example, rotary holding subunit 700, exposure subunit 800). In addition, the processing unit M3 generates information on a wafer W based on data of images taken by the cameras 310, 410, 510.

The instruction unit M4 transmits signals generated by the processing unit M3 to the respective apparatuses. The instruction unit M4 stores the information on the wafer W generated in the processing unit M3 in the storage medium 11*b*. The instruction unit M4 transmits to the storage medium 11*b* an instruction signal for reading out the information on the wafer W stored in the storage medium 11*b*.

Figure 20:
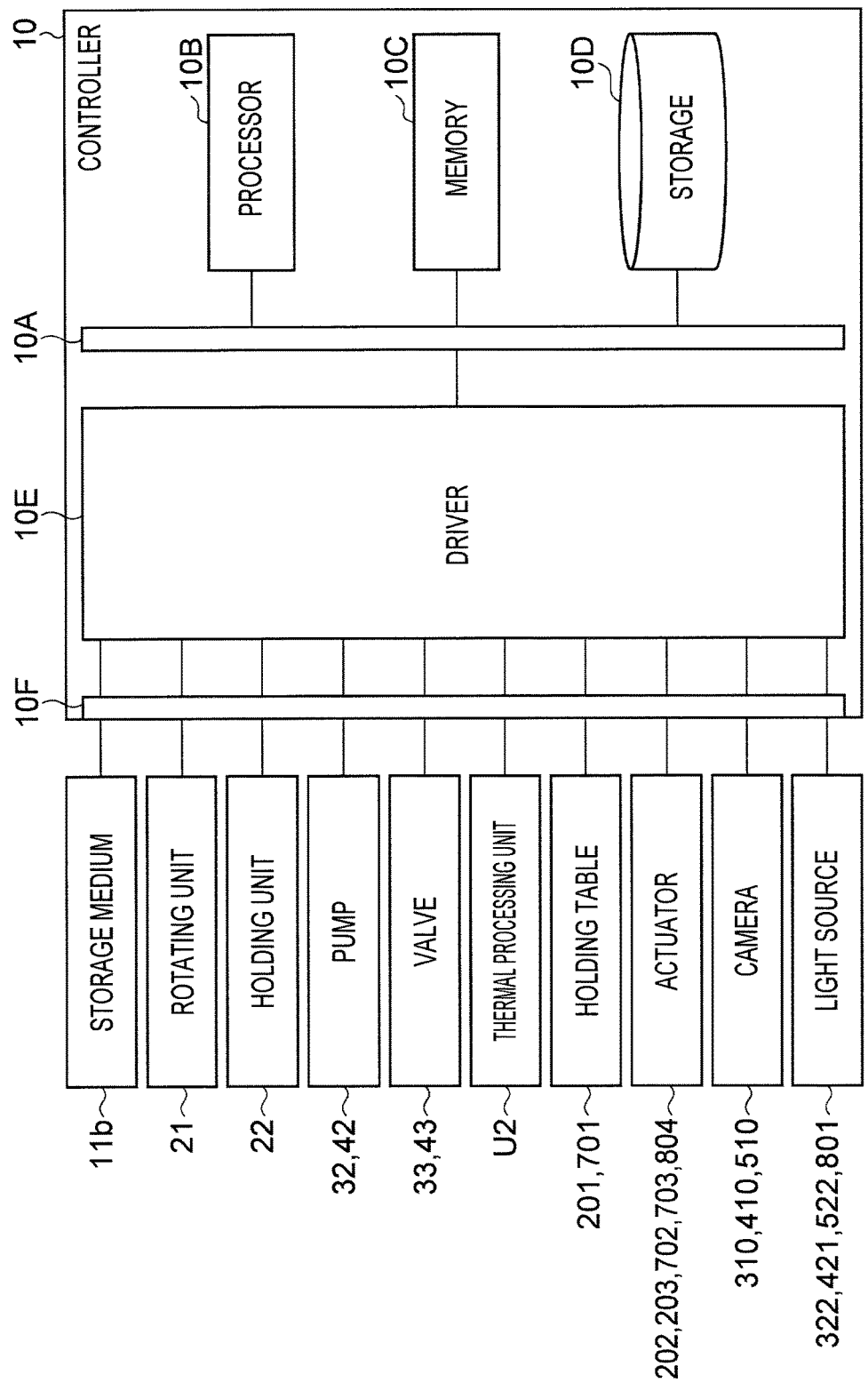
FIG. 20 is a schematic view showing a hardware structure of a controller.

A hardware of the controller 10 is formed of one or more control computer(s), for example. The controller 10 has a circuit 10A as a hardware configuration, which is shown in FIG. 20, for example. The circuit 10A may be formed of an electric circuitry. Specifically, the circuit 10A includes a processor 10B, a memory 10C (storage unit), a storage 10D (storage unit), a driver 10E and an input and output port 10F. The processor 10B cooperates with at least one of the memory 10C and the storage 10D to execute a program, so that a signal is inputted and outputted through the input and output port 10F, whereby the aforementioned respective functional modules are realized. The memory 10C and the storage 10D function as the storage unit M2. The driver 10E is a circuit for driving the respective apparatuses of the substrate processing system 1. Signals are inputted and outputted through the input and output port 10F, between the drive 10E and the various apparatuses of the substrate processing system 1 (for example: storage medium 11*b*; rotating unit 21; holding unit 22, pumps 32, 42; valves 33, 43; thermal processing unit U2; holding tables 201, 701; actuators 202, 203, 702, 703, 804; cameras 310, 410, 510; light sources 322, 421, 522, 801).

In this embodiment, although the substrate processing system 1 has one controller 10, the substrate processing system 1 may have a group of controllers (control unit) formed of the plurality of controllers 10. When the substrate processing system 1 has a group of controllers, the above-described functional modules may be respectively realized by the one controller 10, or may be realized by a combination of two or more computers 10. When the controller 10 is composed of a plurality of computers (circuits 10A), the above-described functional modules may be realized by one computer (circuit 10A), or may be realized by a combination of two or more computers (circuits 10A). The controller 10 may have the plurality of processors 10B. In this case, the above-described functional modules may be respectively realized by one processor 10B, or may be realized by a combination of two or more processors 10B.

<Method of Calculating Profile Line of Reference Wafer>

Figure 21:
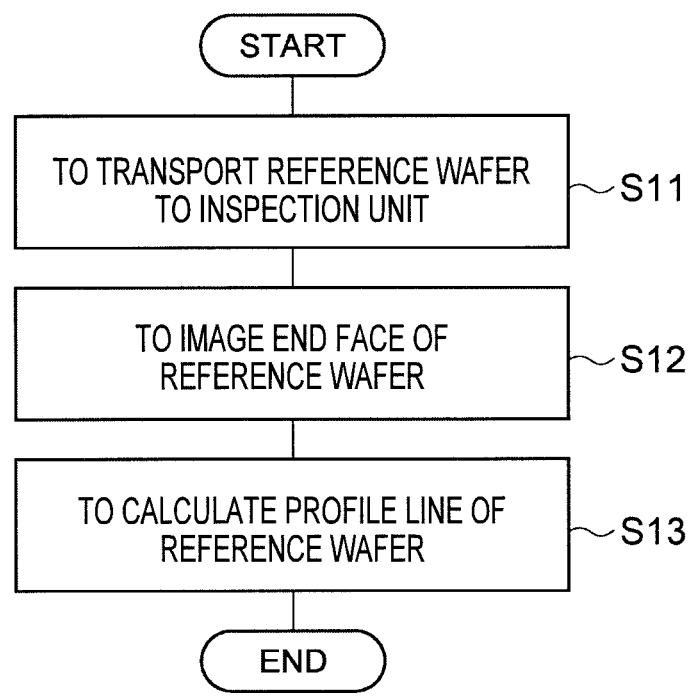
FIG. 21 is a flowchart for explaining a procedure for calculating a profile line of a reference wafer

Next, a method for calculating a profile line of a reference wafer by means of the inspection unit U3 is described with reference to FIG. 21. Herein, the reference wafer means a wafer whose warp amount (in particular, peripheral warp amount) is known. The reference wafer may be a flat wafer. An evaluation index of a flatness of a wafer W may be, for example, GBIR (Global Backside Ideal focal plane Range), SFQR (Site Frontside least Squares focal plane Range), SBIR (Site Backside least Squares focal plane Range), ROA (Roll OffAmount), ESFQR (Edge Site Frontside least Squares focal plane Range), ZDD (Z-height Double Differentiation), etc., which are defined by SEMI (Semiconductor equipment and materials international) standard. The reference wafer may have a flatness in which a maximum value of SFQR is about 100 nm, a flatness in which a maximum value of SFQR is about 42 nm, a flatness in which a maximum value of SFQR is about 32 nm, or a flatness in which a maximum value of SFQR is about 16 nm.

Because of the runout of the rotation shaft of the holding table 201, the assembling error (within the tolerance range) of the rotary holding subunit 200, and the manufacturing error (within the tolerance range) of the suction surface of the holding table 201 and so on, a wafer W rotated by the holding table 201 may rotate eccentrically and the periphery of the wafer W may oscillate vertically. The reference wafer is used to obtain a reference value of the vertical oscillation of a wafer W on the rotary holding subunit 200. Data on the reference value may be obtained by using the reference wafer before a wafer W is processed by the substrate processing system 1. Alternatively, data on the reference value may be obtained by using the reference wafer after maintenance (adjustment, cleaning, etc.) of the substrate processing system 1. Alternatively, data on a reference value may be periodically obtained by using the reference wafer. A precise warp amount of the process wafer can be determined by comparing inspection data on a process wafer W (a wafer to be actually processed obtained) by using the inspection unit U3 with the reference value data.

Firstly, the controller 10 controls the respective units of the substrate processing system 1 such that the reference wafer is transported to the inspection unit U3 (step S11). Then, the controller 10 controls the rotary holding subunit 200 such that the reference wafer is held by the holding table 201. Then, the controller 10 controls the rotary holding subunit 200 such that the holding table 201 is moved by the actuator 203 from the first position to the second position along the guide rail 204. Thus, the peripheral portion of the reference wafer is positioned between the illuminating module 420 and the mirror member 430.

Then, the controller 10 controls the rotary holding subunit 200 to rotate the holding table 201 by the actuator 202, whereby the reference wafer is rotated. Under this condition, the controller 10 controls the periphery imaging subunit 400 such that the light source 421 is turned on and that an image is taken by the camera 410 (step S12). In this manner, the image of an end face of the reference wafer is taken over the whole periphery of the reference wafer.

Figure 25:
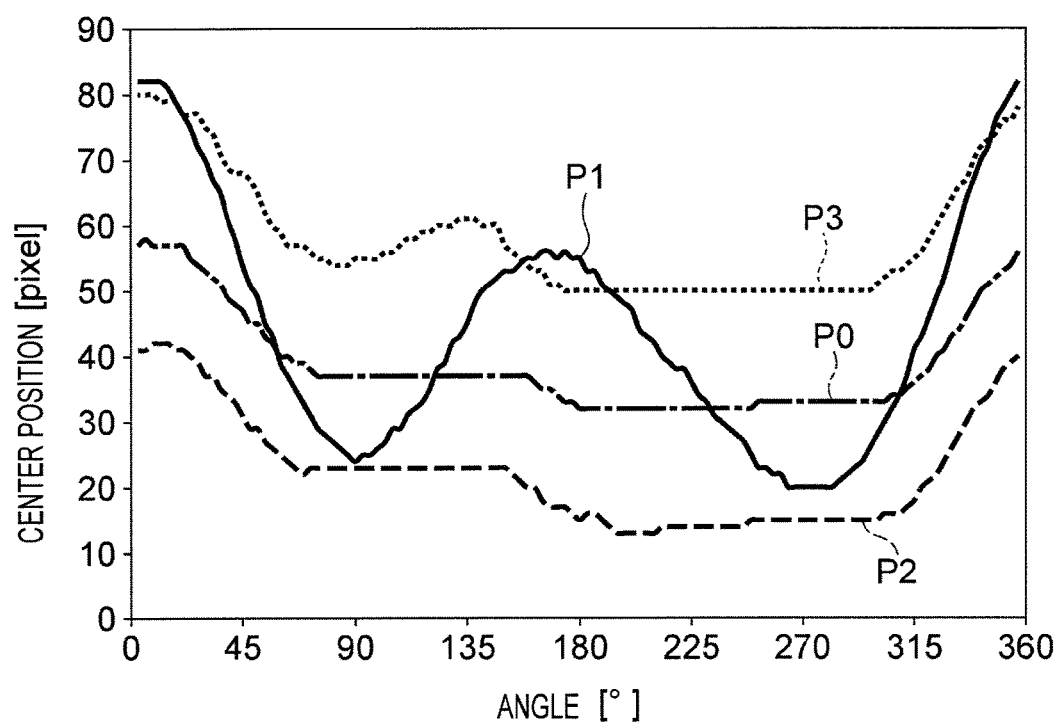
FIG. 25 is a graph showing profile lines of a wafer and a reference wafer.

Then, based on the image of the end face of the reference wafer obtained in the step S12, the profile line of the reference wafer is calculated by the processing unit M3 (step S13). To be specific, the controller 10 makes the processing unit M3 determine the upper edge and the lower edge of the end face of the reference wafer from the image based on the contrast difference, for example. Then, the controller 10 makes the processing unit U3 determine as the profile line a line passing through the median positions between the upper edge and the lower edge. Thus, the shape of the end face of the reference wafer is obtained. FIG. 25 shows a profile line P0 of the reference wafer by way of example.

<Wafer Processing Method>

Figure 22:
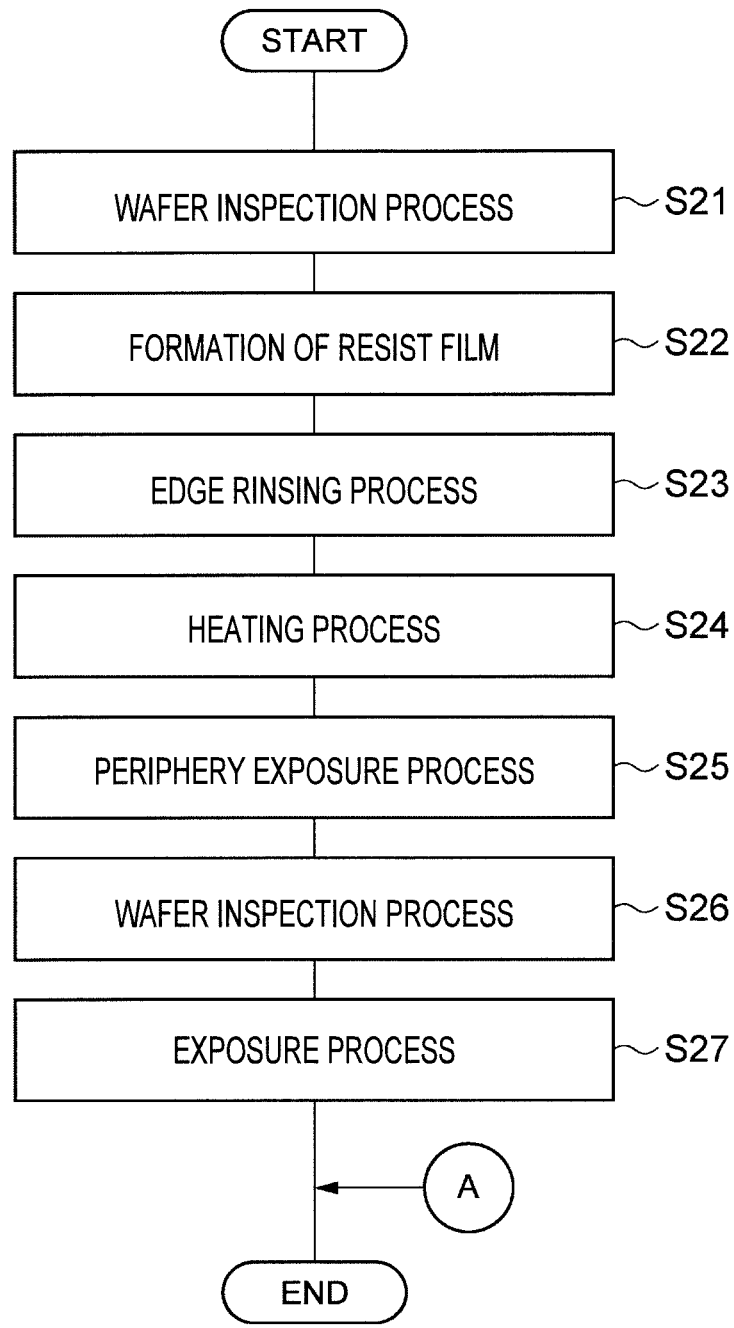
FIG. 22 is a flowchart for explaining an example (first example) of a wafer processing procedure.

Next, a method of processing a wafer W is described with reference to FIG. 22. Firstly, the controller 10 controls the respective units of the substrate processing system 1 such that a wafer W is transported from the carrier 11 to the inspection unit U3 where the wafer W is subjected to an inspection process (step S21). In the inspection process of the wafer W, the warp amount of the wafer W is calculated, details of which will be described later. The calculated warp amount is related to the wafer W and stored in the storage unit M2.

Then, the controller 10 controls the respective units of the substrate processing system 1 such that the wafer W is transported to the liquid processing unit U1 where a resist film R is formed on a front surface Wa of the wafer W (step S22). To be specific, the controller 10 controls the rotary holding unit 20 such that the wafer W is held by the holding unit 22 and that the wafer W is rotated at a predetermined rotating speed. Under this condition, the controller 10 controls the pump 32, the valve 33 and the nozzle 34 (more specifically, the drive unit that drives the nozzle 34) such that the process liquid L1 (resist liquid) is discharged from the nozzle 34 onto the front surface Wa of the wafer W whereby an unsolidified coating film (unsolidified film) is formed all over the front surface Wa of the wafer W.

Then, the controller 10 controls the respective units of the substrate processing system 1 such that a part of the unsolidified film (peripheral portion of the unsolidified film) located at a peripheral portion Wd of the wafer W is removed (a so-called edge rinsing process is performed) (step S23). To be specific, the controller 10 controls the rotary holding unit 20 such that the wafer W is held by the holding unit 22, and that the wafer W is rotated at a predetermined rotating speed (e.g., about 1500 rpm). Under this condition, the controller 10 controls the pump 42, the valve 43 and the nozzle 44 (more specifically, the drive unit that drives the nozzle 44) such that the process liquid L2 (thinner which is an organic solvent) is discharged from the nozzle 44 onto the peripheral portion Wd of the front surface Wa of the wafer W whereby the peripheral portion of the unsolidified film is dissolved.

Then, the controller 10 controls the respective units of the substrate processing system 1 such that the wafer W is transported from the liquid processing unit U1 to the thermal processing unit U2. Then, the controller 10 controls the thermal processing unit U2 such that the unsolidified film together with the wafer W is heated (so-called PAB) whereby the unsolidified film is solidified to be a solidified film (resist film R) (step S24).

Figure 24A:
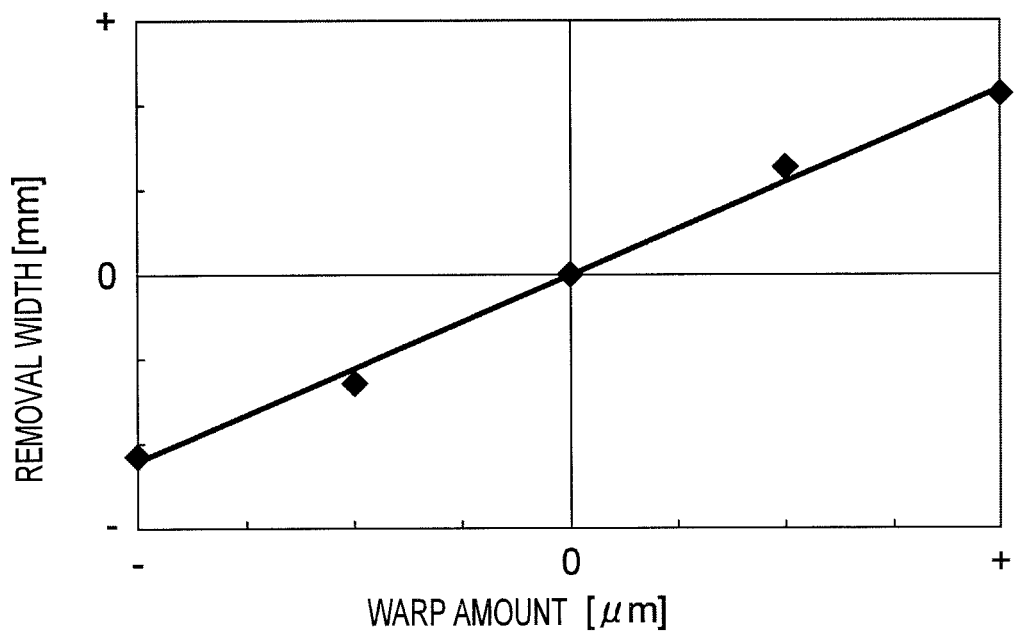
FIG. 24A is a graph showing a relationship between a warp amount of a wafer and a removal width of a peripheral portion of a resist film.
Figure 24B:
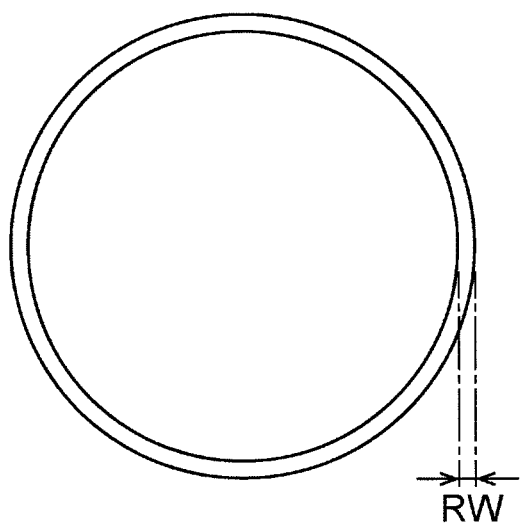
FIG. 24B is a diagram for explaining the removal width of the peripheral portion of the resist film.

If the periphery of the wafer W is warped, the height position of the periphery of the wafer W may vary during the rotation of the wafer W. An edge rinsing test was conducted to a wafer W having a warped periphery, without changing the height position of the nozzle 44. From this test, as shown in FIG. 24A, it was confirmed that there is a proportional relationship between the warp amount of the periphery of the wafer W and the removal width RW (see FIG. 24B) of the peripheral portion of the resist film R. Thus, if such a wafer W is subjected to the edge rinsing process, the removal width RW may be non-uniform along the periphery of the wafer W. The removal width RW is a linear distance between the periphery of the wafer W and the periphery of the resist film R measured in the radial direction of the wafer W, when seen from the side of the front surface Wa of the wafer W.

Thus, in the step S23, the controller 10 reads out the warp amount of the periphery of the wafer W, which was calculated in the step S21, from the storage unit M2, and determines, based on the warp amount, parameter values such as the supply position from which the process liquid L2 is to be supplied by the nozzle 44 to the peripheral portion of the resist film R. Since the setting value of the removal width is set beforehand in the process recipe of the liquid processing unit U1 on the assumption that the wafer W is not warped, the controller 10 corrects the setting value based on the warp amount, such that the actual removal width of the peripheral portion of the unsolidified film corresponds to a desired value. To be specific, the controller 10 controls the nozzle 44 such that the position of the discharge port of the nozzle 44 is adjusted, or controls the nozzle 44 such that the moving speed of the nozzle 44 relative to the wafer W is adjusted, or controls the valve 43 such that the discharge flow rate of the process liquid L2 from the nozzle 44 is adjusted, in order that the removal width of the peripheral portion of the unsolidified film corresponds to the desired value.

In this manner, the process liquid L2 (organic solvent) is discharged from the nozzle 44 onto the peripheral portion Wd of the front surface Wa of each of the different wafers W, while changing the parameter values such as the supply position from which the process liquid L2 is to be supplied by the nozzle 44. When one wafer W is subjected to the edge rinsing process, since the rotating speed of the wafer W in the edge rinsing process is relatively high (e.g., about 1500 rpm), the supply position may be determined based on the average of warp amounts of the periphery of the wafer W. The removal width may be, e.g., about 1 mm.

Then, the controller 10 controls the respective units of the substrate processing system 1 such that the wafer W is transported from the liquid processing unit U1 to the periphery exposure unit U4 where the wafer W is subjected to a periphery exposure process (step S25). To be specific, the controller 10 controls the rotary holding subunit 700 such that the wafer W is held by the holding table 701 and that the wafer W is rotated at a predetermined rotating speed (e.g., about 30 rpm). Under this condition, the controller 10 controls the exposure subunit 800 such that the light source 801 emits predetermined energy beam (ultraviolet ray) to the resist film R located at the peripheral portion Wd of the front surface Wa of the wafer W. If the center axis of the holding table 701 and the center axis of the wafer W do not coincide with each other, the wafer W is eccentrically rotated on the holding table 701. In this case, the controller 10 may control the actuator 703 such that the holding table 701 moves along the guide rail 704 depending on the eccentric amount of the wafer W.

When the periphery of the wafer W is warped, the height position of the periphery of the wafer W may vary during the rotation of the wafer W. In this case, when the peripheral portion Wd of the front surface Wa of the wafer W is irradiated with energy beam, the peripheral portion Wd may have areas on which the energy beam converges and areas on which the energy beam does not converge. Thus, the exposure amount of the peripheral portion Wd may be insufficient.

Thus, in the step S25, the controller 10 reads out the warp amount of the periphery of the wafer W, which is calculated in the step S21, and determines, based on the warp amount, the position of the exposure subunit 800 relative to the peripheral portion Wd. Since the setting value of the exposure width is set beforehand in the process recipe of the periphery exposure unit U4 on the assumption that the wafer W is not warped, the controller 10 corrects the setting value based on the warp amount, such that the actual exposure width of the peripheral portion of the resist film R corresponds to a desired value. To be specific, the controller 10 controls the actuator 703 such that the horizontal position of the wafer W relative to the exposure subunit 800 is adjusted, or controls actuator 804 to adjust the gap (optical path length) between the wafer W and the exposure subunit 800, in order that the exposure width of the peripheral portion of the resist film R corresponds to the desired value. For example, if the periphery of the wafer W is warped to approach the exposure subunit 800 (warped upward), the horizontal position of the wafer W relative to the exposure subunit 800 is adjusted such that the exposure subunit 800 approaches center of the wafer W, or the exposure subunit 800 is moved upward. On the other hand, if the periphery of the wafer W is warped to be removed from the exposure subunit 800 (warped downward), the horizontal position of the wafer W relative to the exposure subunit 800 is adjusted such that the exposure subunit 800 approaches the periphery of the wafer W, or the exposure subunit 800 is moved downward. For example, when the periphery of the wafer W is warped at about 200 μm, the horizontal position of the wafer W relative to the exposure subunit 800 is adjusted at about 0.1 mm, for example, or the height position of the exposure subunit 800 with respect to the wafer W is adjusted at about 0.2 mm, for example.

In this manner, the peripheral portion Wd of the front surface Wa of each of the wafers W is irradiated with the energy beam, while changing the position of the exposure subunit 800 relative to the wafer W. When one wafer W is subjected to the periphery exposure process, since the rotating speed of the wafer W is relatively low (e.g., about 30 rpm), the position of the exposure subunit 800 relative to the wafer W may be determined based on the warp amount relative to coordinates of the periphery of the wafer W. The exposure width is larger than the removal width in the edge rinsing process, and may be, e.g., about 1.5 mm.

Then, the controller 10 controls the respective units of the substrate processing system 1 such that the wafer W is transported from the periphery exposure unit U4 to the inspection unit U3 where the wafer W is subjected to an inspection process (step S26). The inspection process of the wafer W in this step is the same as that of the step S21, and details thereof will be described later.

Then, the controller 10 controls the respective units of the substrate processing system 1 such that the wafer W is transported from the inspection unit U3 to the exposure apparatus 3 where the wafer W is subjected to an exposure process (step S27). To be specific, in the exposure apparatus 3, the resist film R formed on the front surface Wa of the wafer W is irradiated with predetermined energy beam in a predetermined pattern. Thereafter, a resist pattern is formed on the front surface Wa of the wafer W through a developing process in the unit processing block 17.

<Wafer Inspection Method>

Figure 23:
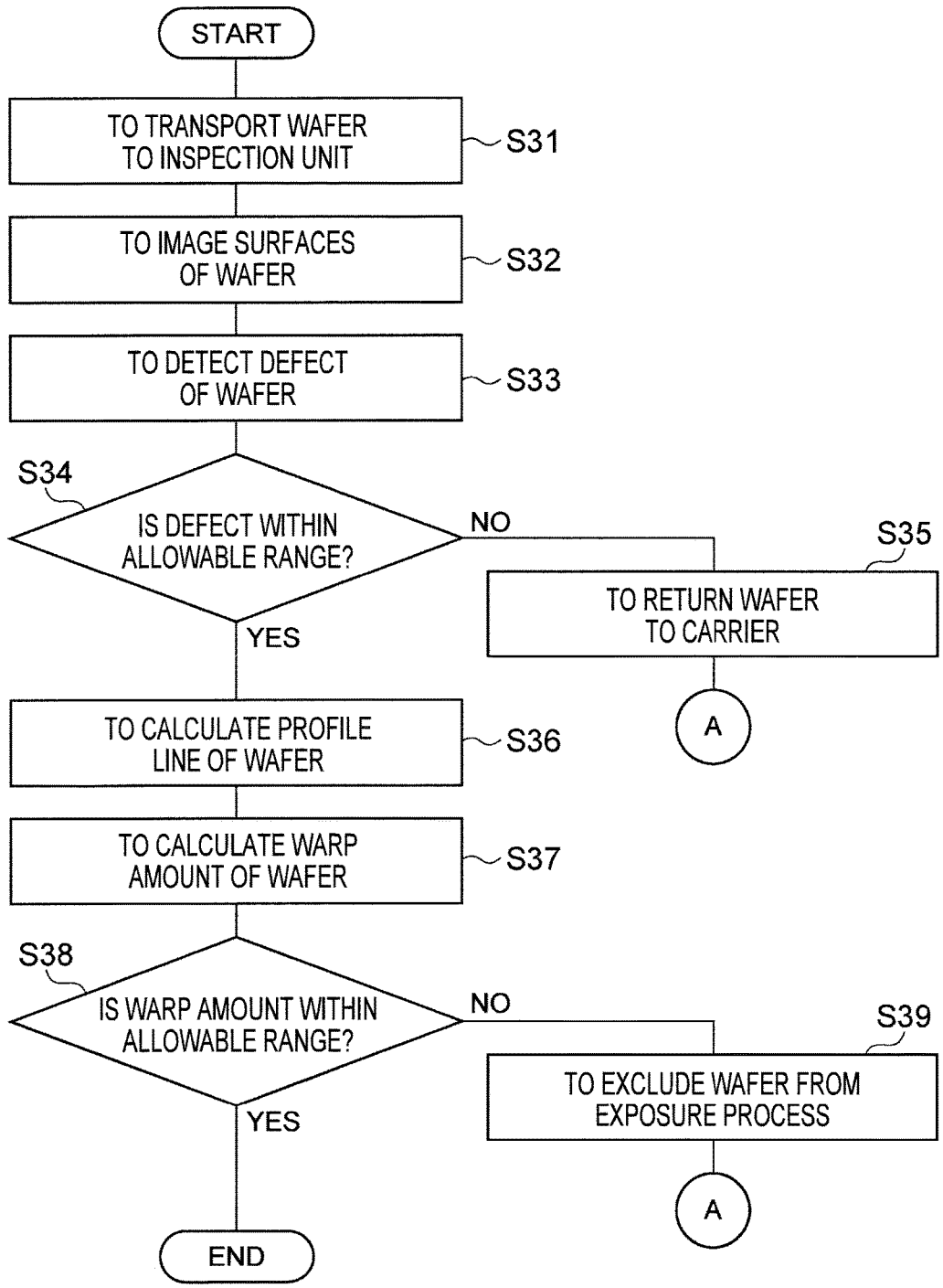
FIG. 23 is a flowchart for explaining a wafer inspection procedure.

A method of inspecting a wafer W (process substrate) is described in detail with reference to FIG. 23. Firstly, the controller 10 controls the respective units of the substrate processing system 1 such that the wafer W is transported to the inspection unit U3 (step S31). Then, the controller 10 controls the rotary holding subunit 200 such that the wafer W is held by the holding table 201. Then, the controller 10 controls the rotary holding subunit 200 such that the holding table 201 is moved by the actuator 203 from the first position to the second position along the guide rail 204. At this time, the controller 10 controls the front surface imaging subunit 300 such that the light source 322 is turned on and that an image is taken by the camera 310 (step S32; an imaging step of the front surface Wa of the wafer W). Thus, the whole front surface Wa of the wafer W is imaged. When the wafer W reaches the second position and the imaging by the camera 310 is completed, data of the image taken by the camera 310 are transmitted to the storage unit M2. Upon completion of the imaging by the camera 310, the peripheral portion of the wafer W is positioned between the illuminating module 420 and the mirror member 430.

Then, the controller 10 controls the rotary holding subunit 200 such that the holding table 201 is rotated by the actuator 202. Thus, the wafer W is rotated. Under this condition, the controller 10 controls the periphery imaging subunit 400 such that the light source 421 is turned on and that an image is taken by the camera 410 (step S32; an imaging step of the end face Wc of the wafer W and an imaging step of the peripheral portion Wd of the front surface Wa of the wafer W). Thus, the end face Wc of the wafer W and the peripheral portion Wd of the front surface Wa of the wafer W are imaged over the whole periphery of the wafer W. At the same time, the controller 10 controls the rear surface imaging subunit 500 such that the light source 522 is turned on and that an image is taken by the camera 510 (step S32; an imaging step of the rear surface Wb of the wafer W). After the wafer W has been rotated for one rotation so that the imaging by the cameras 410, 510 is completed, data of the images taken by the cameras 410, 510 are transmitted to the storage unit M2.

Then, the controller 10 makes the processing unit M3 process the data of the images, which are taken in the step S32, so as to detect defects of the wafer W (step S33). The defect detection by the image processing can be performed in various ways, and defects may be detected based on the contrast difference, for example. The controller 10 makes the processing unit M3 judge the type of the defect (for example, flaw, crack, scratch, insufficient formation of the coating film, etc.) based on the size, the shape, the location, etc., of the defect.

Then, the controller 10 makes the processing unit M3 judge whether the defect detected in the step S33 is allowable or not. If it is judged that the wafer W has an unallowable defect (NO in step S34), the wafer W is not subjected to a succeeding process, and the controller 10 controls the respective units of the substrate processing system 1 such that the wafer W is returned to the carrier 11 (step S35). Thus, the wafer W is not subjected to the exposure process in the step S26 (see mark "A" in FIGS. 22 and 23).

On the other hand, if it is judged that the wafer W has no defect or the wafer W has an allowable defect (YES in step S34), the controller 10 makes the processing unit M3 calculate a profile line of the wafer W based on the image of the end face Wc of the wafer W obtained in the step S32 (step S36). To be specific, the controller 10 recognizes the upper edge and the lower edge of the end face Wc of the wafer W from the image based on the contrast difference, for example. Then, the controller 10 makes the processing unit U3 determine, as a profile line, a line passing through the median positions between the upper edge and the lower edge. Thus, the shape of the end face Wc of the wafer W is obtained.

By way of example, FIG. 25 shows three types of profile lines P1 to P3 of the wafer W. The profile line P1 is like a sine curve that intersects the profile line P0 of the reference wafer. The profile line P2 extends along and below the profile line P0 of the reference wafer. The profile P3 extends along and above the profile line P0.

Then, the controller 10 makes the processing unit M3 calculate the warp amount of the wafer W by correcting the profile line P1 to P3 obtained in the step S36 using the profile line P0 that is obtained in the step S13 (step S37). To be specific, the controller 10 makes the processing unit M3 calculate the difference of the profile line of the wafer W from the profile line of the reference wafer (i.e., subtracting the profile line of the reference wafer from the profile line of the wafer W) so as to calculate the warp amount of the wafer W at each coordinate value (i.e., each angular position).

Figure 26:
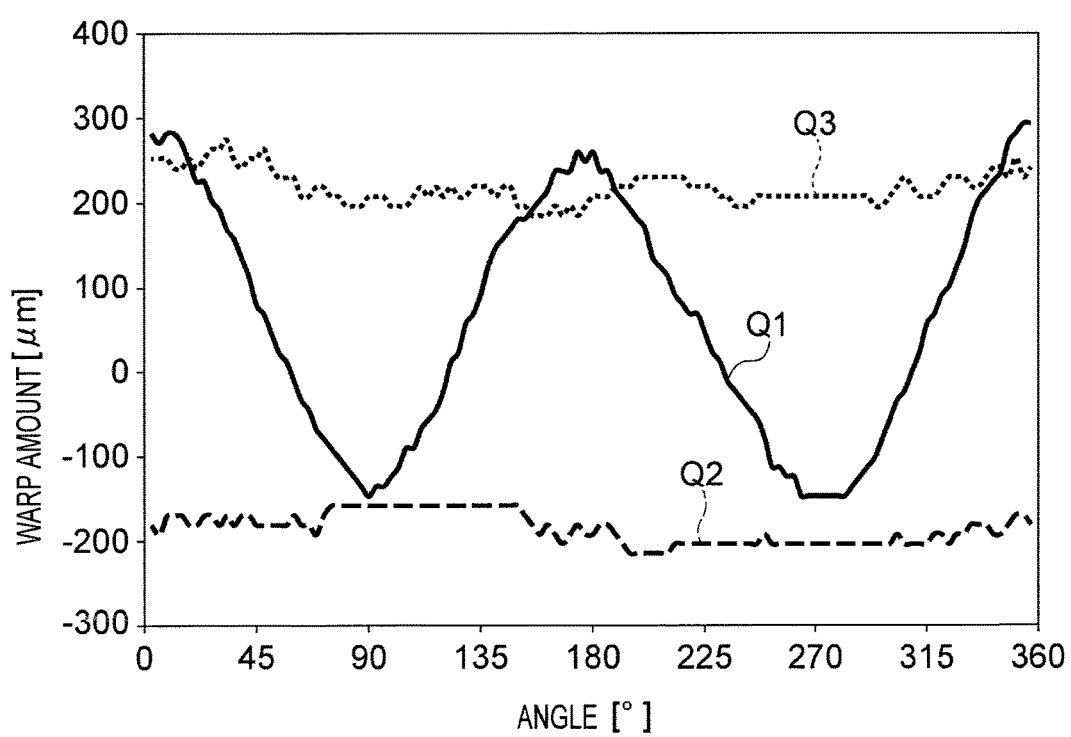
FIG. 26 is a graph showing a warp amount.
Figure 27A:
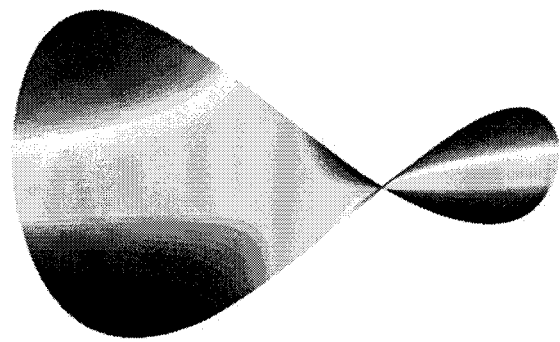
FIG. 27A is a perspective view showing a wafer having a hyperbolic paraboloid shape.
Figure 27B:
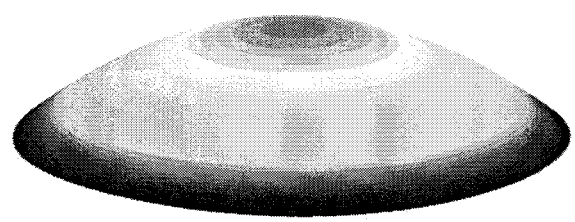
FIG. 27B is a perspective view showing a wafer having an upwardly convex paraboloid of revolution shape.
Figure 27C:
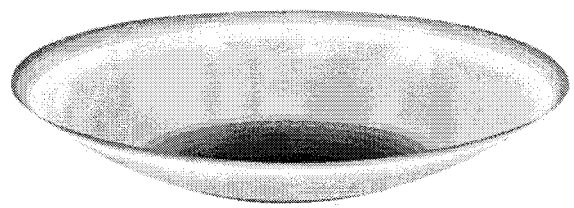
FIG. 27C is a perspective view showing a wafer having a downwardly convex paraboloid of revolution shape.

FIG. 26 shows a warp amount Q1 which is obtained by subtracting the profile line P0 of the reference wafer from the profile line P1 of the wafer W, a warp amount Q2 which is obtained by subtracting the profile line P0 of the reference wafer from the profile line P2 of the wafer W, and a warp amount Q3 which is obtained by subtracting the profile line P0 of the reference wafer from the profile line P3 of the wafer W. From the warp amount Q1, it can be understood that the periphery of the wafer W undulates up and down. Thus, it can be judged that the wafer W has a hyperbolic paraboloid shape as shown in FIG. 27A. From the warp amount Q2, it can be understood that the periphery of the wafer W is lowered. Thus, it can be judged that the wafer W has an upwardly convex paraboloid of revolution shape as shown in FIG. 27B. From the warp amount Q3, it can be understood that the periphery of the wafer W is raised. Thus, it can be judged that the wafer W has a downwardly convex paraboloid of revolution shape as shown in FIG. 27C.

Then, the controller 10 makes the processing unit M3 judge whether the warp amount obtained in the step S37 is within an allowable range or not. An allowable range of the warp amount may be set by a numerical value in an overlay (OL) control of the exposure apparatus 3. If it is judged that the warp amount is too large to allow (NO in step S38), the controller 10 makes the storage unit M2 store information that the wafer W is not subjected to the exposure process, in relation to the wafer W (step S39). Thus, the wafer W is not subjected to the exposure process in the step S26 (see mark "A" in FIGS. 22 and 23).

On the other hand, if it is judged that the warp amount is small and allowable (YES in step S38), the controller 10 completes the inspection process. At this time, the controller 10 controls the respective units of the substrate processing system 1 such that the wafer W is transported from the inspection unit U3 to the exposure apparatus 3.

<Operation>

In this embodiment, the step S37 calculates the warp amount of the wafer W, and the step S23 determines, based on the warp amount, the supply position from which the process liquid L2 is to be supplied by the nozzle 44 to the peripheral portion of the resist film R, and dissolves the peripheral portion by the process liquid L2 supplied from the supply position so as to remove the same from the wafer W. Thus, since the supply position of the process liquid L2 to the peripheral portion of the resist film R suitable for the warp amount of the periphery of the wafer W can be properly set, the removal width RW of the peripheral portion can be made more uniform. As a result, even if the wafer W is warped, the periphery of the wafer W can be properly processed. In addition, since circuits can be formed on the front surface Wa of the wafer W in areas close to the periphery, higher integration of circuits on the wafer W is promoted whereby the wafer W can be more efficiently utilized.

Similarly, in this embodiment, the step S37 calculates the warp amount of the wafer W, and the step S25 determines the exposure width based on the warp amount. Thus, since the exposure width suitable for the warp amount of the periphery of the wafer W can be properly determined, the exposure width of the peripheral portion can be made more uniform. Thus, the removal width of the peripheral portion of the resist film R can be made more uniform. As a result, even if the wafer W is warped, the periphery of the wafer W can be properly processed. In addition, since circuits can be formed on the front surface Wa of the wafer W in areas close to the periphery, higher integration of circuits on the wafer W is promoted whereby the wafer W can be more efficiently utilized.

In this embodiment, the step S37 calculates the warp amount of the wafer W by correcting the profile line P1 to P3 of the wafer W by using the profile line P0 of the reference wafer. Thus, by subtracting the profile line P0 of the reference wafer from the profile line P1 to P3 of the wafer W, the warp amount of the wafer W can be easily calculated from the profile line P0 and the profile line P1 to P3.

In this embodiment, whether the warp amount obtained in the step 37 is within an allowable range or not is judged. If the warp amount is too large to allow (NO in step S38), the wafer W is not subjected to the exposure process. Namely, a wafer W that is difficult to be exposed by the exposure apparatus 3 can be discriminated beforehand and the wafer W can be excluded from the exposure process. Thus, the process efficiency of wafer W can be improved.

In this embodiment, whether the defect detected in the step S33 is within an allowable range or not is judged. If the wafer W has an unallowable defect (NO in step S34), the wafer W is not subjected to a succeeding process. Namely, the defect (for example, flaw, crack, scratch, etc.) on the front surface Wa of the wafer W or in the vicinity of the periphery of the wafer W can be detected, and the wafer W can be excluded from various processes. Thus, the process efficiency of wafer W can be improved.

In this embodiment, the size of the holding unit 22, the size of the holding table 201 and the size of the holding table 701 are substantially the same. Thus, stresses induced in parts between each of the holding unit 22, the holding table 201 and the wafer W are substantially the same. Thus, when the warp amount of the wafer W is calculated in the step S37, when the edge rinsing process is performed in the step S23, and when the periphery exposure process is performed in the step S25, variation of the warp amount is about the same. As a result, it is easy to correct the setting value of the removal width in the step S23, and to correct the setting value of the exposure width in the step S25, based on the warp amount calculated in the step S37.

In this embodiment, the mirror member 43 has the reflecting surface 432 that is inclined with respect to the rotation axis of the holding table 201, and that opposes the end face Wc and the peripheral portion Wd of the back surface Wb of the wafer W held by the holding table 201. In addition, in this embodiment, the imaging device 412 of the camera 410 receives two light beams through the lens 411, one coming from the peripheral portion Wd of the front surface Wa of the wafer W held by the holding table 201, and the other coming from the end face of the wafer W held by the holding table 201 to fall on the reflecting surface 432 of the mirror member 430 and then being reflected by the reflecting surface 432 of the mirror member 430. Thus, both the peripheral portion Wd of the front surface Wa of the wafer W and the end face Wc of the wafer W are simultaneously imaged by the one camera 410. Thus, since a plurality of cameras are no longer necessary, a space for installation of these cameras is unneeded. In addition, since a mechanism for moving the camera 410 is unnecessary, a space for installation of the mechanism is unneeded. Thus, in this embodiment, the inspection unit U3 can have a significantly simplified structure. As a result, the inspection unit U3 can achieve reduction in size and decrease in cost, while avoiding equipment failure.

In this embodiment, the reflecting surface 432 is a curved surface that is recessed away from the end face Wc of the wafer W held by the holding table 201. Thus, the mirror image of the end face Wc of the wafer W reflected on the reflecting surface 432 is enlarged. For example, if the reflecting surface 432 is not a curved surface, the end face Wc of the wafer W in the image on the imaging device has a width corresponding to about 20 pixels. On the other hand, if the reflecting surface 432 is a curved surface as described above, the width of the end face Wc of the wafer W in the image on the imaging device is enlarged about 1.5 times in the thickness direction. Thus, a more detailed image of the end face Wc of the wafer W can be obtained. As a result, by processing the detailed image, the end face Wc of the wafer W can be more precisely inspected.

The optical path length of the light, which comes from the end face Wc of the wafer W and is reflected by the reflecting surface 432 of the mirror member 430 to reach the lens 411, is longer than the optical path length of the light, which comes from the peripheral portion Wd of the front surface Wa of the wafer W to reach the lens 411, because of the reflection by the mirror member 430. However, in this embodiment, the focus adjusting lens 427 is disposed in the light path extending from the reflecting surface 432 of the mirror member 430 to the lens 411. The focus adjusting lens 427 is configured to adjust an image forming position, at which the image of the end face Wc of the wafer W is formed, onto the imaging device 412. Thus, owing to the focus adjusting lens 427, the image forming position of the end face Wc of the wafer W can be adjusted onto the imaging device 412, whereby both the images of the peripheral portion Wd of the front surface Wa of the wafer W and the end face Wc of the wafer W are clear. As a result, by processing the clear image, the end face Wc of the wafer W can be more precisely inspected.

In this embodiment, the illuminating module 420 irradiates the reflecting surface 432 of the mirror member 430 with diffused light in order to allow the diffused light, which comes from the illuminating module 420 and then is reflected by the reflecting surface 432 of the mirror member 430, to fall on the end face Wc of the wafer W held by the holding table 201. Thus, the diffused light enters the end face Wc of the wafer W from various directions. Thus, the entire end face Wc of the wafer W can be uniformly illuminated. As a result, the end face Wc of the wafer W can be imaged more clearly.

In this embodiment, the light emitted from the light source 421 is scattered by the light scattering member 422, enlarged by the cylindrical lens 425 and further diffused by the light diffusing member 426. Thus, the diffused light enters the end face Wc of the wafer W from various directions. Thus, the entire end face Wc of the wafer W can be uniformly illuminated. As a result, the end face Wc of the wafer W can be imaged more clearly.

<Other Embodiments>

The embodiment according to the disclosure has been described in detail, but the above embodiment can be variously modified within the scope of the present invention. For example, the reflecting surface 432 has another shape (e.g., flat surface) other than a curved face, as long as the reflecting surface 432 is inclined with respect to the rotation axis of the holding table 201 and opposes the end surface Wc and the back surface Wb of the wafer W held by the holding table 201.

The focus adjusting lens 427 may be omitted from the periphery imaging subunit 400.

Any of the light scattering member 422, the cylindrical lens 425 and the light diffusing member 426 may be omitted from the periphery imaging subunit 400.

The inspection unit U3 may be disposed in the shelf units U10, U11. For example, the inspection unit U3 may be provided in the cells of the shelf units U10, U11, which are located correspondingly to the unit processing units 14 to 17. In this case, a wafer W is directly delivered to the inspection unit U3 by the arms A1 to A8 that transport the wafer W.

For the purposed of calculating the warp amount of the wafer W, an imaging module capable of imaging only the end face Wc of the wafer W may be used, without using the periphery imaging subunit 400 capable of imaging both the end face Wc of the wafer W and the peripheral portion Wd of the front surface Wa thereof. The front surface Wa of the wafer W, the rear surface Wb thereof, the end face Wc thereof and the peripheral portion Wd of the front surface Wa thereof may be imaged by different cameras. At least images of two of the front surface Wa of the wafer W, the rear surface Wb thereof, the end face Wc thereof and the peripheral portion Wd of the front surface Wa thereof may be simultaneously taken by one camera.

Before and after the heating process of the step S24, the wafer inspection process may be performed in the same inspection unit U3, or the wafer inspection process may be performed in the different inspection units U3.

The inspection process of the wafer W in the step S25 may be performed, not after the periphery exposure process in the step S24, but after the heating process in the thermal heating unit U2 in the step S22 (so-called PAB) and after the exposure process in the step S26.

Figure 28:
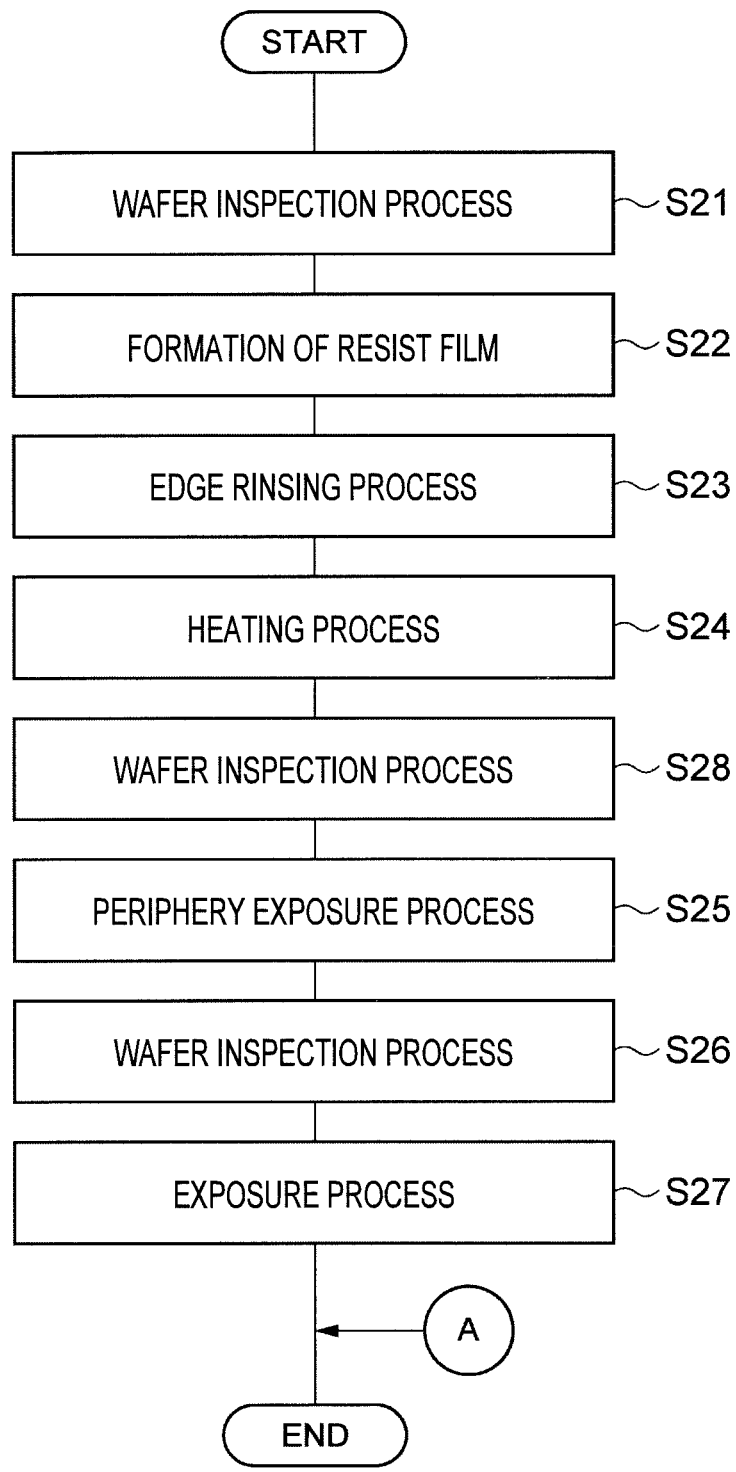
FIG. 28 is a flowchart for explaining another example (second example) of the wafer processing procedure.

As shown in FIG. 28, the wafer inspection process (re-inspection process) (step S28) may be performed by the inspection unit U3 between the heating process in the step S24 and the periphery exposure process in the step S25. At this time, the periphery exposure process in the step S25 may determine the exposure width based on the warp amount calculated by the wafer inspection process in the step S28. In this case, since the exposure width can be more properly determined depending on the warp of the wafer W having been subjected to the heating process in the step S24, the exposure width of the peripheral portion of the resist film R can be made more uniform. Thus, by developing the wafer W after the periphery exposure process, the removal width of the peripheral portion can be made more uniform. In addition, at this time, whether the warp amount calculated by the wafer inspection process in the step S28 is within an allowable range or not may be judged. If the warp amount is too large to allow, the wafer W is not subjected to the exposure process. Namely, a wafer W that is difficult to be exposed by the periphery exposure unit U4 can be discriminated beforehand and the wafer W can be excluded from the periphery exposure process. Thus, the process efficiency of wafer W can be improved.

Figure 29:
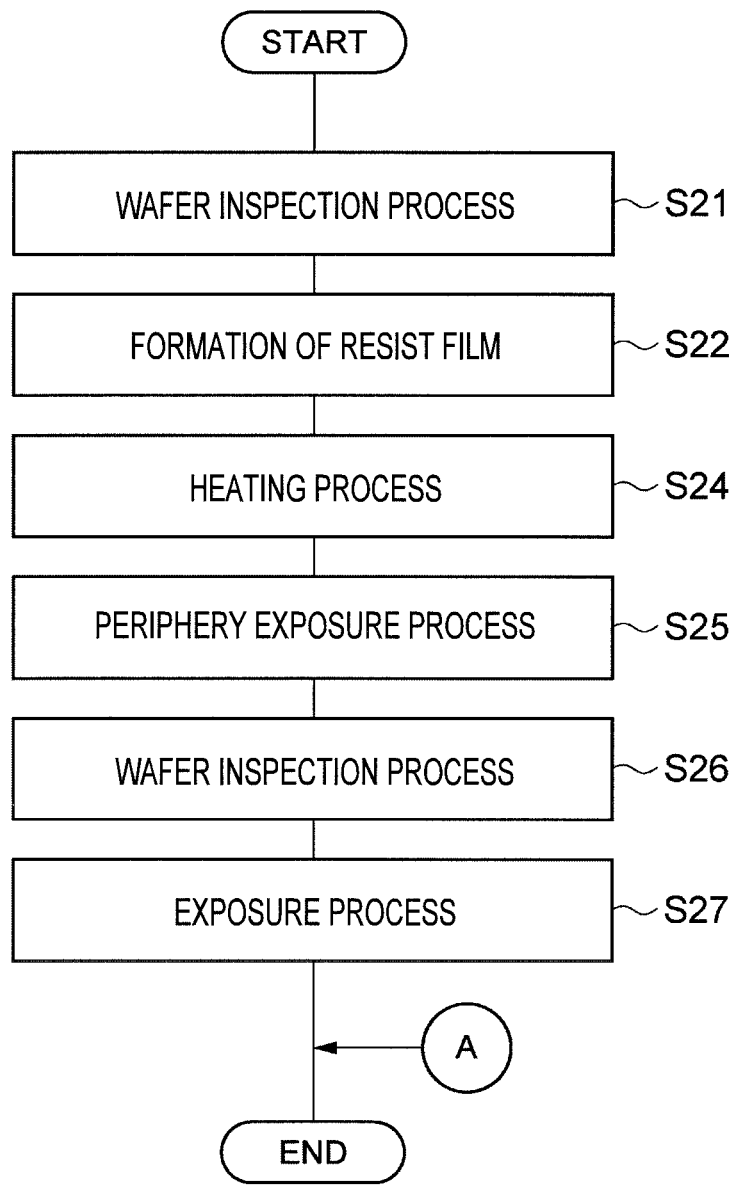
FIG. 29 is a flowchart for explaining yet another example (third example) of the wafer processing procedure.

As shown in FIG. 29, the steps S24 to S27 may be performed without performing the edge rinsing process of the step S23. Although not shown, after performing the heating process of the step S24, the succeeding steps of S26 and S27 may be performed without performing the periphery exposure process of the step S25.

The warp amount calculated by the wafer inspection process (S21) in the inspection unit U2 may be utilized in the succeeding heating process (step S24) in the thermal processing unit U2. For example, judgment on whether the wafer W is to be sucked to the heating plate of the thermal processing unit U2, and controlling of the suction amount, the suction position, the suction pressure, the suction timing and so on may be performed based on the warp amount.

What is claimed is:
1. A substrate processing method comprising:
a first step that takes an image of an end face of a reference substrate, whose warp amount is known, over a whole periphery of the reference substrate by means of a camera;
a second step that performs image processing of the image taken in the first step, thereby to obtain shape data of the end face of the reference substrate over a whole periphery of the reference substrate;
a third step that takes an image of an end face of a process substrate over a whole periphery of the process substrate by means of a camera;
a fourth step that performs image processing of the image taken in the third step, thereby to obtain shape data of the end face of the process substrate over a whole periphery of the process substrate;

a fifth step that calculates a warp amount of the process substrate based on the shape data obtained in the second step and the shape data obtained in the fourth step;

a sixth step that supplies a coating liquid to a surface of the process substrate thereby to form a coating film on the surface of the process substrate;

a seventh step that determines a supply position from which an organic solvent is to be supplied to a peripheral portion of the coating film, based on the warp amount calculated in the fifth step, and supplies the organic solvent from the supply position to dissolve the peripheral portion of the coating film and remove the same from the process substrate.

2. The method according to claim 1, further comprising a periphery exposure step that exposes, after the seventh step, the coating film in the peripheral portion of the surface of the process substrate at a predetermined exposure width over the whole periphery of the process substrate, wherein in the periphery exposure step the exposure width is determined based on the warp amount calculated in the fifth step.

3. The method according to claim 1, further comprising:
an eighth step that heats the coating film after the seventh step;
a ninth step that takes, after the eighth step, an image of the end face of the process substrate over the whole periphery of the process substrate by means of a camera;
a tenth step that performs image processing of the image taken in the ninth step, thereby to obtain shape data of the end face of the process substrate over the whole periphery of the process substrate; and
an eleventh step that calculates a warp amount of the process substrate based on the shape data obtained in the second step and the shape data obtained in the tenth step;
wherein the method does not perform exposure of the process substrate if the warp amount calculated in the eleventh step is greater than a threshold value.

4. The method according to claim 1, further comprising:
an eighth step that heats the coating film after the seventh step;
a ninth step that takes, after the eighth step, an image of the end face of the process substrate over the whole periphery of the process substrate by means of a camera;
a tenth step that performs image processing of the image taken in the ninth step, thereby to obtain shape data of the end face of the process substrate over the whole periphery of the process substrate; and
an eleventh step that calculates a warp amount of the process substrate based on the shape data obtained in the second step and the shape data obtained in the tenth step;
a periphery exposure step that exposes, after the ninth step, the coating film in the peripheral portion of the surface of the process substrate at a predetermined exposure width over the whole periphery of the process substrate, wherein in the periphery exposure step the exposure width is determined based on the warp amount calculated in the eleventh step.

5. The method according to claim 4, wherein the method does not perform exposure of the process substrate if the warp amount calculated in the eleventh step is greater than a threshold value.

6. The method according to claim 1, wherein:
the reference substrate is flat;
the shape data obtained in the second step is data on a first profile line passing through a center of the end face of the reference substrate;
the shape data obtained in the fourth step is data on a second profile line passing through a center of the end face of the process substrate; and
the fifth step calculates the warp amount of the process substrate based on the data on the first profile line and the data on the second profile line.

7. The method according to claim 1, further comprising:
a peripheral portion imaging step that takes an image of a peripheral portion of a surface of the process substrate by means of a camera; and
an inspecting step that inspects condition of the end face of the process substrate through image processing of the image taken in the fourth step, and inspects condition of the peripheral portion of the surface of the process substrate through image processing of the image taken in the peripheral portion imaging step.

8. A non-transitory storage medium storing a program that makes a substrate processing apparatus execute a substrate processing method according to claim 1.

9. A substrate processing method comprising:
a first step that takes an image of an end face of a reference substrate, whose warp amount is known, over a whole periphery of the reference substrate by means of a camera;
a second step that performs image processing of the image taken in the first step, thereby to obtain shape data of the end face of the reference substrate over a whole periphery of the reference substrate;
a third step that takes an image of an end face of a process substrate over a whole periphery of the process substrate by means of a camera;
a fourth step that performs image processing of the image taken in the third step, thereby to obtain shape data of the end face of the process substrate over a whole periphery of the process substrate;
a fifth step that calculates a warp amount of the process substrate based on the shape data obtained in the second step and the shape data obtained in the fourth step;
a sixth step that supplies a coating liquid to a surface of the process substrate thereby to form a coating film on the surface of the process substrate; and
a periphery exposure step that exposes the coating film in the peripheral portion of the surface of the process substrate at a predetermined exposure width over the whole periphery of the process substrate, wherein in the periphery exposure step the exposure width is determined based on the warp amount calculated in the fifth step.

10. The method according to claim 9, further comprising a seventh step that heats the coating film after the sixth step, wherein the third, fourth and fifth steps are performed after the seventh step.

11. The method according to claim 10, wherein the method does not perform exposure of the process substrate if the warp amount calculated in the fifth step is greater than a threshold value.

12. The method according to claim 9, wherein:
the reference substrate is flat;
the shape data obtained in the second step is data on a first profile line passing through a center of the end face of the reference substrate;

the shape data obtained in the fourth step is data on a second profile line passing through a center of the end face of the process substrate; and the fifth step calculates the warp amount of the process substrate based on the data on the first profile line and the data on the second profile line.

13. The method according to claim 9, further comprising:

a peripheral portion imaging step that takes an image of a peripheral portion of a surface of the process substrate by means of a camera; and an inspecting step that inspects condition of the end face of the process substrate through image processing of the image taken in the fourth step, and inspects condition of the peripheral portion of the surface of the process substrate through image processing of the image taken in the peripheral portion imaging step.

14. A non-transitory storage medium storing a program that makes a substrate processing apparatus execute a substrate processing method according to claim 9.

* * * * *